US010168332B2

(12) United States Patent
Oh

(10) Patent No.: US 10,168,332 B2
(45) Date of Patent: Jan. 1, 2019

(54) METHOD FOR PREDICTING PROGNOSIS OF ACUTE MYELOID LEUKEMIA RELAPSE

(71) Applicant: The Catholic University of Korea Industry-Academic Cooperation Foundation, Seoul (KR)

(72) Inventor: Il Hoan Oh, Seoul (KR)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 15/307,002

(22) PCT Filed: Apr. 28, 2015

(86) PCT No.: PCT/KR2015/004233
§ 371 (c)(1),
(2) Date: Oct. 27, 2016

(87) PCT Pub. No.: WO2015/167210
PCT Pub. Date: Nov. 5, 2015

(65) Prior Publication Data
US 2017/0045517 A1    Feb. 16, 2017

(30) Foreign Application Priority Data

Apr. 28, 2014 (KR) ........................ 10-2014-0050613
Apr. 28, 2015 (KR) ........................ 10-2015-0059550

(51) Int. Cl.
*G01N 33/574* (2006.01)
*C12Q 1/6886* (2018.01)
*G01N 33/50* (2006.01)

(52) U.S. Cl.
CPC ..... *G01N 33/57426* (2013.01); *C12Q 1/6886* (2013.01); *G01N 33/5044* (2013.01); *G01N 2800/54* (2013.01)

(58) Field of Classification Search
CPC . G01N 33/574; G01N 33/5044; C12Q 1/6886
USPC ....................................................... 435/7.23
See application file for complete search history.

(56) References Cited

U.S. PATENT DOCUMENTS

2012/0070450 A1    3/2012   Ishikawa et al.
2013/0079424 A1    3/2013   Gerber et al.

FOREIGN PATENT DOCUMENTS

WO    WO 2015/167210    11/2015

OTHER PUBLICATIONS

Ground of Reasons of Rejection dated Nov. 17, 2016 From the Korean Intellectual Property Office Re. Application No. 10-2015-0059550. (4 Pages).
Blau "Bone Marrow Stromal Cells in the Pathogenesis of Acute Myeloid Leukemia", Frontiers in Bioscience, 19: 171-180, Jan. 1, 2014.
Supplementary European Search Report and the European Search Opinion dated Dec. 6, 2017 From the European Patent Office Re. Application No. 15785551.1. (10 Pages).
Hanoun et al. "Acute Myeloid Leukemia Alters the Mesenchymal Stem Cell Potential of the HSC Niche: Evidence for Modulation by Beta-Adrenergic Signals", Blood, XP055427841, 122(21): 342, Nov. 15, 2013. Last P.
Kim et al. "Microenvironmental Remodeling as a Parameter and Prognostic Factor of Heterogeneous Leukemogenesis in Acute Myelogenous Leukemia", Cancer Research, XP055427273, 75(11): 2222-2231, Published Online Mar. 18, 2015.
International Search Report and the Written Opinion dated Jul. 3, 2015 From the Korean Intellectual Property Office Re. Application No. PCT/KR2015/004233 and Its Translation of Search Report Into English.
Manabe et al. "Bone Marrow-Derived Stromal Cells Prevent Apoptotic Cell Death in B-Lineage Acute Lymphoblastic Leukemia", Blood, 79(9): 2370-2377, May 1, 1992. Abstract.
Mudry et al. "Stromal Cells Regulate Survival of B-Linkeage Leukemic Cells During Chemotherapy", Blood, 96(5): 1926-1932, Sep. 1, 2000. Abstract.
Ning et al. "The Correlation Between Cotransplantation of Mesenchymal Stem Cells and Higher Recurrence Rate in Hematologic Malignancy Patients: Outcome of a Pilot Clinical Study", Leukemia, 22(3): 593-599, Published Online Jan. 10, 2008. Abstract.
Rodriguez-Pardo et al. "Mesenchymal Stem Cells Promote Leukaemic Cells Aberrant Phenotype From B-Cell Acute Lymphoblastic Leukaemia", Hematology Oncology and Stem Cell Therapy, 6(3-4): 89-100, 4th Quarter 2013. Abstract, p. 90, 97, 98.

*Primary Examiner* — Yan Xiao

(57) ABSTRACT

The present invention relates to a method for predicting the prognosis of acute myeloid leukemia relapse. According to the present invention, the prognosis of acute myeloid leukemia relapse can be predicted by analyzing changes in a bone marrow microenvironment during the early diagnosis of leukemia.

18 Claims, 26 Drawing Sheets

|  | No. Test | Normal Growth | Growth Arrest | No Forming Colony |
|---|---|---|---|---|
| Normal | 11 | 10/11 (90.9%) | 1/11 (9.1%) | 0/11 (0.0%) |
| AML (M1) | 13 | 9/13 (69.2%) | 1/13 (7.7%) | 3/13 (23.1%) |
| AML (M2) | 14 | 8/14 (57.1%) | 4/14 (28.6%) | 2/14 (14.3%) |
| AML (M3) | 9 | 0/9 (0.0%) | 8/9 (88.9%) | 1/9 (11.1%) |
| AML (M4) | 2 | 1/2 (50.0%) | 1/2 (50.0%) | 0/2 (0.0%) |
| AML (M5) | 5 | 4/5 (80.0%) | 1/5 (20.0%) | 0/5 (0.0%) |
| AML (M7) | 1 | 0/1 (0.0%) | 0/1 (0.0%) | 1/1 (100.0%) |
| AML/MD | 7 | 5/7 (71.4%) | 2/7 (28.6%) | 0/7 (0.0%) |

Fig. 2C

Upward-Control in MSCs of Leukemic CD34+

AMINE_TRANSMEMBRANE_TRANSPORTER_ACTIVITY (41)
AMINE_TRANSPORT (38)
AXON_GUIDANCE (22)
CHEMOKINE_RECEPTOR_BINDING (43)
AMINO_ACID_TRANSPORT (26)
CARBOXYLIC_ACID_TRANSMEMBRANE_TRANSPORTER_ACTIVITY (44)
CARBOXYLIC_ACID_TRANSPORT (41)
CHEMOKINE_ACTIVITY (42)
ORGANIC_ACID_TRANSPORT (42)
G_PROTEIN_COUPLED_RECEPTOR_BINDING (54)

Downward-Control in MSCs of Leukemic CD34+

SPINDLE (38)
CHROMOSOME (122)
CHROMATIN_BINDING (32)
CHROMOSOMAL_PART (95)
M_PHASE_OF_MITOTIC_CELL_CYCLE (84)
LYASE_ACTIVITY (69)
REPLICATION_FORK (18)
DNA_DEPENDENT_DNA_REPLICATION (50)
DNA_REPLICATION (94)
CELL_CYCLE_PHASE (166)

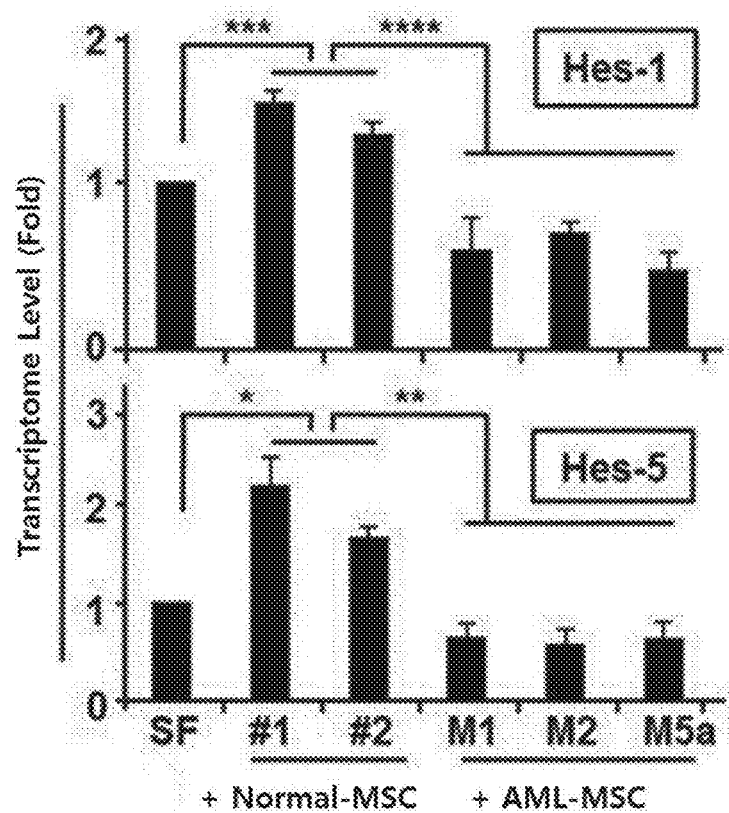

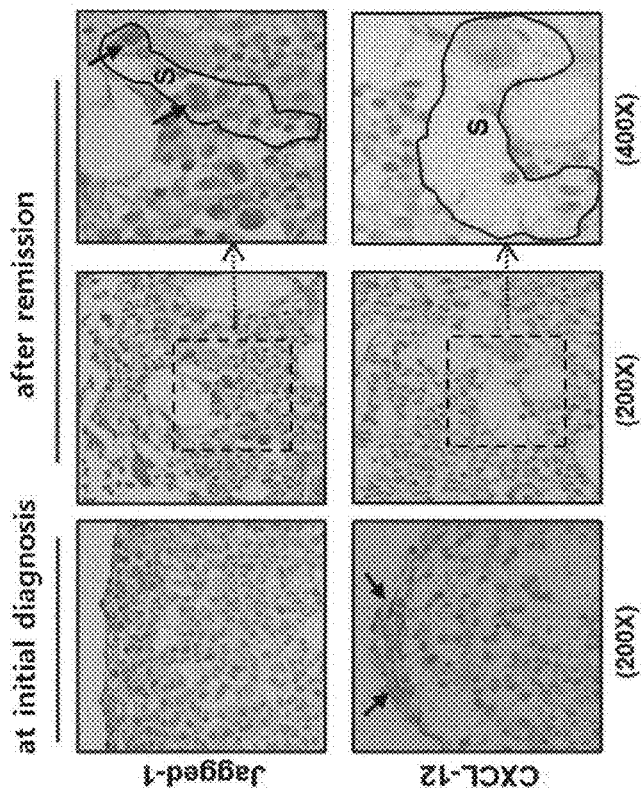
Fig. 3H
Fig. 4A
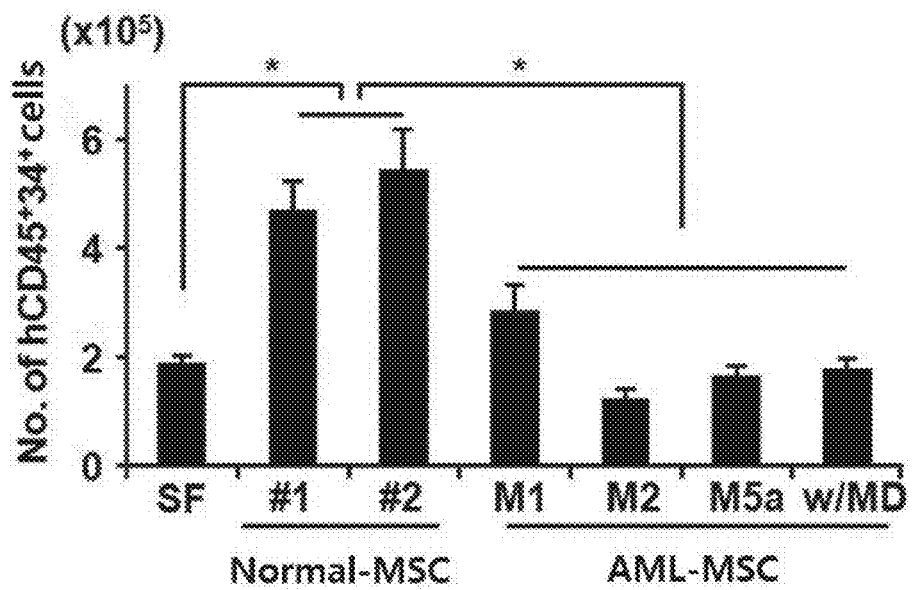

| AUC (se) | MSC | EC | P-MSC | OB | CPU-F |
|---|---|---|---|---|---|
| Relapse vs. CR (total) | 0.78 (0.07) | 0.63 (0.09) | 0.72 (0.09) | 0.70 (0.09) | 0.69 (0.09) |
| Early Relapse within 1yr vs. CR | 0.73 (0.09) | 0.65 (0.09) | 0.80 (0.08) | 0.63 (0.11) | 0.73 (0.10) |
| Late Relapse after 1yr vs. CR | 0.91 (0.06) | 0.57 (0.15) | 0.52 (0.25) | 0.88 (0.08) | 0.59 (0.18) |

Fig. 5B

METHOD FOR PREDICTING PROGNOSIS OF ACUTE MYELOID LEUKEMIA RELAPSE

RELATED APPLICATIONS

This application is a National Phase of PCT Patent Application No. PCT/KR2015/004233 having International filing date of Apr. 28, 2015, which claims the benefit of priority of Korean Patent Applications Nos. 10-2014-0050613 filed on Apr. 28, 2014 and 10-2015-0059550 filed on Apr. 28, 2015. The contents of the above applications are all incorporated by reference as if fully set forth herein in their entirety.

FIELD AND BACKGROUND OF THE INVENTION

The present invention relates to a method for predicting prognosis of acute myeloid leukemia relapse.

Leukemia is a generic term for disorders that leukocytes proliferate into tumors. Types of leukemia are classified as myeloid leukemia and lymphocytic leukemia according to the leukocytes originating leukemia and as acute leukemia and chronic leukemia in accordance with the progress rate. Clinical profiles of leukemia vary depending on the type of diseases and nature of the affected cells. Lymphocytic leukemia is caused when lymphoid blood cells are mutated, myeloid leukemia is caused when myeloid blood cells are mutated, chronic myeloid leukemia is caused when cells in the mature stage are mutated, and acute myeloid leukemia (AML) is caused by disorder of myeloblasts starting differentiation in a relatively early state of the hematopoietic process. Acute myeloid leukemia mainly occurs in adults, the elderly, where children patients are about 10 to 15% of the entire leukemia patients. Acute lymphocytic leukemia mainly occurs in children, which is known to have the highest incidence in 2-10 year children. Chronic myeloid leukemia has a high incidence in the old age of 60s or older and chronic lymphocytic leukemia is a rare leukemia in Korea. Acute myeloid leukemia is known to account for about 70% of all the acute leukemia.

The treatment of acute myeloid leukemia includes chemotherapy, radiation therapy, or hematopoietic stem cell transplantation therapy, and the initial diagnosis usually leads to a complete remission by chemotherapy. If the therapy after the initial diagnosis reaches to the complete remission, no leukemia cell can be found on bone marrow and blood tests, but there are theoretically still at least 100 million leukemic cells in vivo. Thus, the acute myeloid leukemia has also a high risk of recurrence after the complete remission, so that it is important to predict prognosis of relapse about the acute myeloid leukemia after the complete remission.

SUMMARY OF INVENTION

Accordingly, the present invention is intended to provide a marker for prognostic prediction of acute myeloid leukemia relapse, a method for predicting prognosis of acute myeloid leukemia relapse using the marker and a method for providing information for prognostic prediction of acute myeloid leukemia relapse.

The present invention provides a method for providing information for prognostic prediction of acute myeloid leukemia, which comprises analyzing the composition of stromal cells in a bone marrow sample obtained from an individual.

The present invention also provides a method for predicting prognosis of acute myeloid leukemia, which comprises analyzing the composition of stromal cells in a bone marrow sample obtained from an individual.

According to the present invention, it is possible to predict prognosis of acute myeloid relapse by analyzing microenvironment changes of bone marrow on initial diagnosis of leukemia.

BRIEF DESCRIPTION OF THE SEVERAL VIEWS OF THE DRAWINGS

FIG. 2C shows the most important 10 GO categories upwardly- and downwardly-controlled, in MSCs co-cultured with leukemia $CD34^+$ cells, as compared to MSCs co-cultured with normal $CD34^+$ cells.

FIG. 3C shows the effect that the co-culture with normal or AML-MSC affects on down-stream notch signals. This represents mean folds ±SEM of transcriptomes compared with levels in stroma-free (SF) conditions Non-substrate (SF) (three repeated experiments, n=3 per each group).

FIG. 3H shows the result analyzing the expression change of jagged-1 or CXCL-12 in the BM compartment of AML patients by immunohistochemistry at the initial diagnosis and after remission. The portion indicated by 'S' refers to the positively stained portion near to BM sinusoids in reticular cells. In addition, the arrow refers to the positively stained portion, and the dotted line portion refers to the area enlarged at a high magnification (400×).

FIG. 4A shows the total expansion amount of CD34$^+$ cells when normal CD34$^+$ cells of umbilical cord blood are cultured in stroma-free conditions (SF) for 5 days or co-cultured on two normal donor(#1, #2)-derived MSCs or four AML patient-derived leukemic MSCs (three timed repeated experiments, mean SEM, n=7 per each group, *p<0.05).

FIG. 5B shows the result analyzing AUC values of the BM stromal cell composition, in order to verify the efficacy as biomarkers for predicting acute myeloid leukemia relapse of the BM stromal cell composition (the case of AUS value>0.8 or more is indicated by the box).

DESCRIPTION OF SPECIFIC EMBODIMENT OF THE INVENTION

Figure 1A:
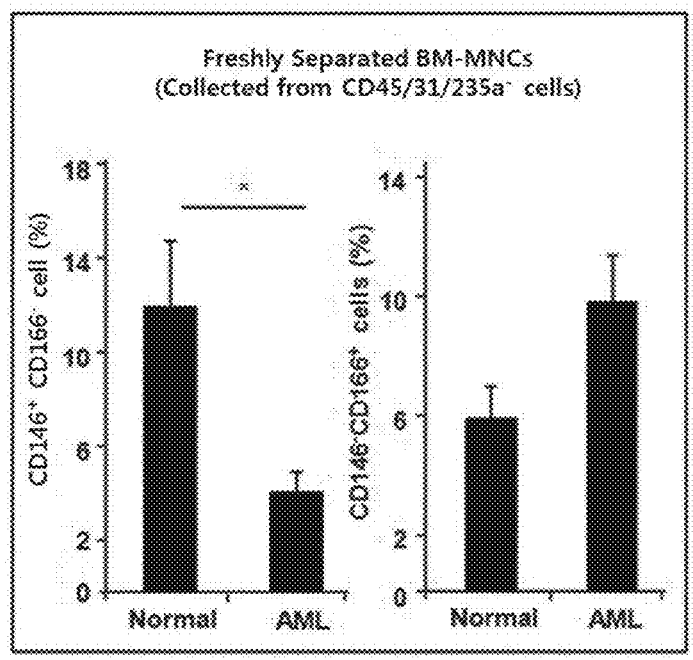
FIG. 1A shows a comparison result of the composition of mesenchymal cells from bone marrows of normal donors and AML patients (mean±SEM (standard error of the mean), n=51 for AML, n=11 for normal donors).

It is known that the onset of acute myeloid leukemia (AML) is associated with a change in the microenvironment of the bone marrow. When leukemic cells are created due to mutation of hematopoietic stem cells (HSCs), the leukemic cells and leukemic stem cells (LSCs) cause changes in the surrounding microenvironment to create and maintain leukemic conditions. The present inventors confirmed through the following examples that when these LSCs similar to normal HSCs were transplanted in mice, they competed with niches of normal HSCs and moreover the leukemic cells transplanted in mice formed bone marrow niches to change the transplanted normal HSCs into tumor niches.

First, to confirm whether the bone marrow microenvironment of patients with acute myeloid leukemia is different from the normal individual, the compositions of the mesenchymal stromal cells in the leukemic bone marrow and the normal bone marrow were analyzed and compared (Example 1). The significant loss of mesenchymal progenitors (M-progenitors) appeared in the acute myeloid leukemic bone marrow over the normal bone marrow, but mature osteoblastic cells (OBs) were increased. In addition, in the acute myeloid leukemic bone marrow, a decrease of colony forming capacity and proliferation capacity appeared and an increase of β-galactosidase activity appeared. This shows that in the leukemic bone marrow, mesenchymal differentiation was changed.

In order to confirm whether the change in the bone marrow microenvironment as above is due to the leukemic cells, the gene expression profiles in mesenchymal stromal cells were analyzed, in a group of co-culturing leukemic cells and mesenchymal stromal cells and a case of co-culturing normal cells and mesenchymal stromal cells (Example 2). As a result, in the group of co-culturing with leukemic cells, an increase of gene expression related to cytokines, and a decrease of gene expression related to cell cycle or proliferation, and the like appeared. In addition, to confirm whether the leukemic cells cause remodeling of niche cross-talk, the expression profile of cross-talk molecules was analyzed (Example 2). As a result, in the mesenchymal stromal cells co-cultured with leukemic cells, the expression decrease of the cross-talk molecules, jagged-1, and the expression increase of CXCL-12 could be confirmed. These results suggest that the leukemic cells cause change of niches.

Furthermore, to evaluate whether such change of niches affects on function of hematopoietic cells, the effects on normal hematopoietic and leukemic function were analyzed. As a result, due to change of niches by the leukemic cells, it could be confirmed that normal hematopoiesis action is suppressed. Besides, it could be known that the change of niches by the leukemic cells acts in a direction to raise the resistance to apoptosis of the leukemic cells and the resistance to chemical therapy (Example 3). This suggests that the leukemia cells remodel stroma so as to be favorable to survival of the leukemic cells themselves, while destroying normal hematopoiesis action.

Based on the above results, the present inventors have hypothesized that, in acute myeloid leukemia, leukemia cells change niches of bone marrows, such change of niches changes the microenvironment in the bone marrows, and such change of the microenvironment is associated with prognosis of acute myeloid leukemia relapse. The present invention was accomplished by confirming it through the following examples that the above hypothesis is appropriate.

Thus, the present invention provides a method for providing information for prognostic prediction of acute myeloid leukemia relapse which comprises analyzing change of the microenvironment within the bone marrow sample obtained from an individual. The present invention also provides a method for predicting prognosis of acute myeloid leukemia relapse which comprises analyzing change of the microenvironment within the bone marrow sample obtained from an individual. The change of the microenvironment in the bone marrow can be confirmed by analyzing the composition of stromal cells in the bone marrow.

In the present invention, stromal cells means connective tissue cells of the bone marrow, which include primitive mesenchymal stromal cells (P-MSCs), differentiated mesenchymal stromal cells (MSCs), osteoblastic cells (OB), and the like.

In one embodiment, the analysis of the composition of stromal cells may include analyzing one or more levels selected from the group consisting of primitive mesenchymal stromal cells, differentiated mesenchymal stromal cells and osteoblastic cells in the bone marrow sample obtained from the individual. In one example of the invention, primitive mesenchymal stromal cells, differentiated mesenchymal stromal cells and osteoblastic cells function as a marker for prognostic prediction of acute myeloid leukemia relapse. The level of primitive mesenchymal stromal cells, differentiated mesenchymal stromal cells and osteoblastic cells can be analyzed by checking the number of each cell. The composition of the stromal cells can be readily analyzed by flow cytometry, and the like, which is carried out on bone marrow examination for diagnosing acute myeloid leukemia.

In one example of the invention, the individual may be an individual for initial diagnosis of leukemia as a candidate group of acute myeloid leukemia. According to the invention, there is an advantage of being capable of predicting the prognosis of the later relapse at the initial diagnosis of acute myeloid leukemia.

In one embodiment, it may further comprise comparing the composition of stromal cells in the bone marrow sample obtained from a leukemia-free individual. The leukemia-free individual herein refers to the individual in normal state without leukemia and other diseases.

In one embodiment, as a result of comparing data from the candidate group of acute myeloid leukemia with data obtained from the leukemia-free individual, it can be an indicator of the complete remission of acute myeloid leukemia when primitive mesenchymal stromal cells and differentiated mesenchymal stromal cells are reduced in the candidate group. The complete remission herein refers to a case not causing relapse for a period of at least 5 years, or 5 years to 8 years after the first remission determination.

In one embodiment, the increase of primitive mesenchymal progenitor cells may be an indicator of early relapses within one year of acute myeloid leukemia.

In one embodiment, the increase of differentiated mesenchymal stromal cells and/or osteoblastic cells may be an indicator of late relapses after more than one year of acute myeloid leukemia.

As a result of evaluating whether the remodeling of stroma by the leukemic cells is associated with the prognosis of acute myeloid leukemia relapse through the cohort study (Example 4), it could be confirmed that a high number of primitive mesenchymal stromal cells in the bone marrow at the initial diagnosis is highly associated with the early relapse, whereas a high number of differentiated mesenchymal stromal cells or osteoblastic cells is associated with the late relapse. In addition, it could be confirmed that the reduction of primitive mesenchymal stromal cells and differentiated mesenchymal stromal cells is the indicator of the complete remission of acute myeloid leukemia. These results suggest that the early and late relapses of acute myeloid leukemia can be predicted through the microenvironment analysis of stroma at the initial diagnosis of leukemia. According to the present invention, the likelihood of later relapses of acute myeloid leukemia can be predicted by easily analyzing the composition of the stromal cells in the bone marrow by only the bone marrow examination which is performed at the initial diagnosis of leukemia.

Accordingly, the present invention provides a method for analyzing the composition of the stromal cells in the bone marrow to predict the prognosis of acute myeloid leukemia relapse.

The method for analyzing the composition of the bone marrow stromal cells can apply all the content described in the above method for providing information for prognostic prediction of acute myeloid leukemia relapse.

As the leukemic cells affect stroma of the bone marrow, the present invention also a method for inhibiting relapses of acute myeloid leukemia and a method for providing information for inhibiting relapses through inhibition of the interaction between each mesenchymal stromal cell and the leukemic cells by utilizing the fact that the likelihood of relapses of acute myeloid leukemia is high, when there are a large number of primitive mesenchymal stromal cells, differentiated mesenchymal stromal cells and osteoblastic cells, various through the inhibition of the interaction between mesenchymal stromal cells with leukemic cells it provides a method for providing information to a method of inhibiting recurrence and to inhibit the recurrence of acute myeloid leukemia.

The present invention also provides a method for screening a relapse inhibitor of acute myeloid leukemia which comprises treating a candidate material and analyzing whether the candidate material inhibits the interaction of the leukemic cells and the bone marrow stromal cells. When the treated candidate material inhibits the interaction of the leukemic cells and the bone marrow stromal cells compared to the control group of the untreated candidate material, the candidate material can be used as a relapse inhibitor of acute myeloid leukemia.

If the primitive mesenchymal stromal cells increase, the likelihood of the acute myeloid leukemia relapse at the early phase is high, and if the differentiated mesenchymal stromal cells and/or the osteoblastic cells increase, the likelihood of the acute myeloid leukemia relapse at the late phase is high, so that one or more inhibitors selected from the group consisting of inhibitors of primitive mesenchymal stromal cells, differentiated mesenchymal stromal cells and osteoblastic cells may be used as a preventive application of acute myeloid leukemia relapse.

Hereinafter, the present invention will be described in detail through examples. The following examples merely illustrate the present invention, but the scope of the present invention is not limited to the flowing examples.

All data in Examples below were analyzed using Statistical Analysis System (SAS, version 9.3; SAS Institute Inc., Cary, N.C., USA) and a level of significance was set as P<0.05.

EXAMPLE 1

Confirmation of change of the mesenchymal cells in BMs of AML patients

In order to examine the potential changes in the bone marrow microenvironment of leukemia patients, the cell composition of bone marrow stromal cells without pretreatment of the patients first diagnosed with acute myeloid leukemia (AML) was first analyzed.

In all experiments, after receiving the informed consent in accordance with the research approval by the institutional review board of St. Mary's Hospital and Seoul St. Mary's Hospital, the bone marrow samples of the acute myeloid leukemia patients without pretreatment were obtained and used. Light-density mononuclear cells (MNCs) were separated from the bone marrow or leukapheresis samples of the acute myeloid leukemia patients by Ficoll-Paque gradient centrifugation and then cryopreserved for analysis. Umbilical cord blood cells from mothers or bone marrows of normal donors were similarly obtained after informed consent.

As a result of cell composition analysis, in the test of mesenchymal stromal cells (MSCs; CD45−31−235a−) the acute myeloid leukemic bone marrow showed a significant loss of mesenchymal progenitors (M-progenitors; CD45−31−235a−146+166−), the mature osteoblastic cells (OBs; CD45−31−235a−146−166+) increased over the normal bone marrow (FIG. 1A), and this shows that the mesenchymal differentiation has changed.

Figure 1B:
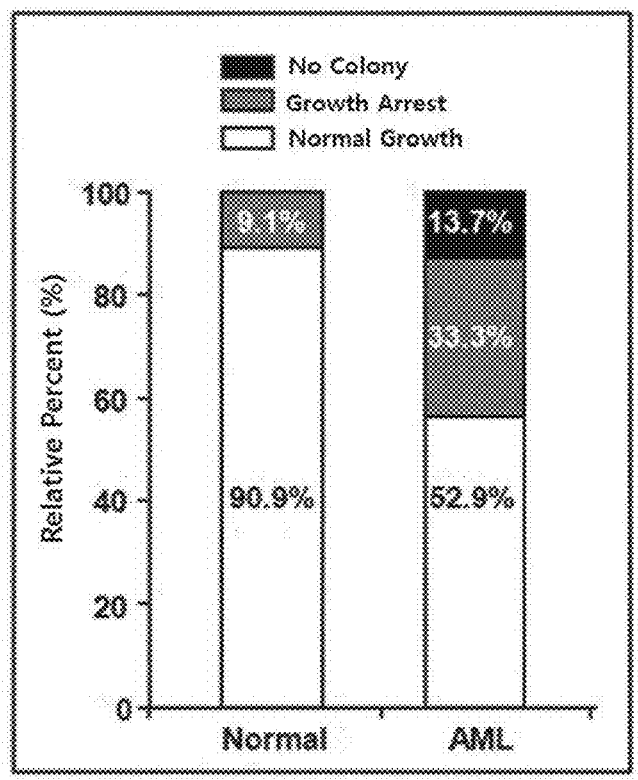
FIG. 1B shows a result comparing colony forming activity and proliferating ability of mesenchymal cells in bone marrows of donors and AML patients (n=51 for AML, n=11 for normal donors).

Furthermore, since the primitive mesenchymal stromal cells are largely expressed to the colony forming cells (CFU-F) including niche cells in the bone marrow, the colony forming and self-renewal capacity of mesenchymal progenitors in normal and leukemic bone marrows was tested. For the CFU-F formation, the BM MNCs were plated for 14 days ($1\times10^6$ cells/plate). Colonies were stained with crystal violet or sub-cultured. Percentages of the BMs with forming no colony (no colony), the BMs reaching growth arrest within two passages (growth arrest) and the BMs continuously proliferating after three passages (normal growth) were shown in FIG. 1B (n=51; AML, n=11; normal BM). Bone marrow mononuclear cells (MNCs) from acute myeloid leukemia patients frequently failed in forming colony (13.7% vs. 0% for the leukemic bone marrow and the normal bone marrow, respectively) and the accelerated growth arrest within two passages of subculture associated with aging-associated β-galactosidase activities appeared as higher frequency than the normal bone marrow (33.3% versus 9.1% for acute myeloid leukemia and normal, respectively) (FIG. 1B).

Also, the colony forming capacity (FIG. 1C) and the proliferation capacity (FIG. 1D) of the mesenchymal cells for the AML subtypes according to the FAB classification were investigated.

Figures 1C, 1D:
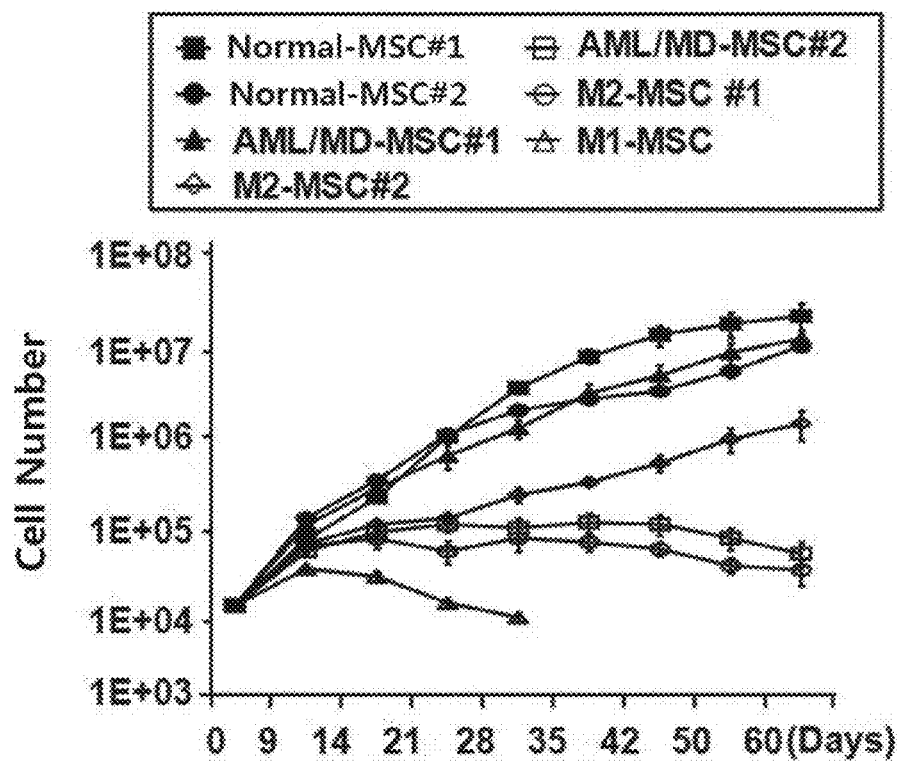
FIG. 1C shows a variation of mesenchymal cells in BMs of the patient according to the AM1 subtype by the FAB classification.
FIG. 1D shows the number of AML-MSCs representing normal growth of being continually proliferated through two passages during subculture in vitro for 60 days (n=2 for normal donors, n=5 for AML patients).

As a result, the change of the mesenchymal stromal cell function in acute myeloid leukemia patients was observed regardless of the subtypes of acute myeloid leukemia (FIG. 1C). More frequent decreases of proliferation were observed during subculture of 60 days even for the acute myeloid leukemia-derived mesenchymal stromal cells (AML-MSCs) showing growth after three passages (FIG. 1D).

Figure 1E:
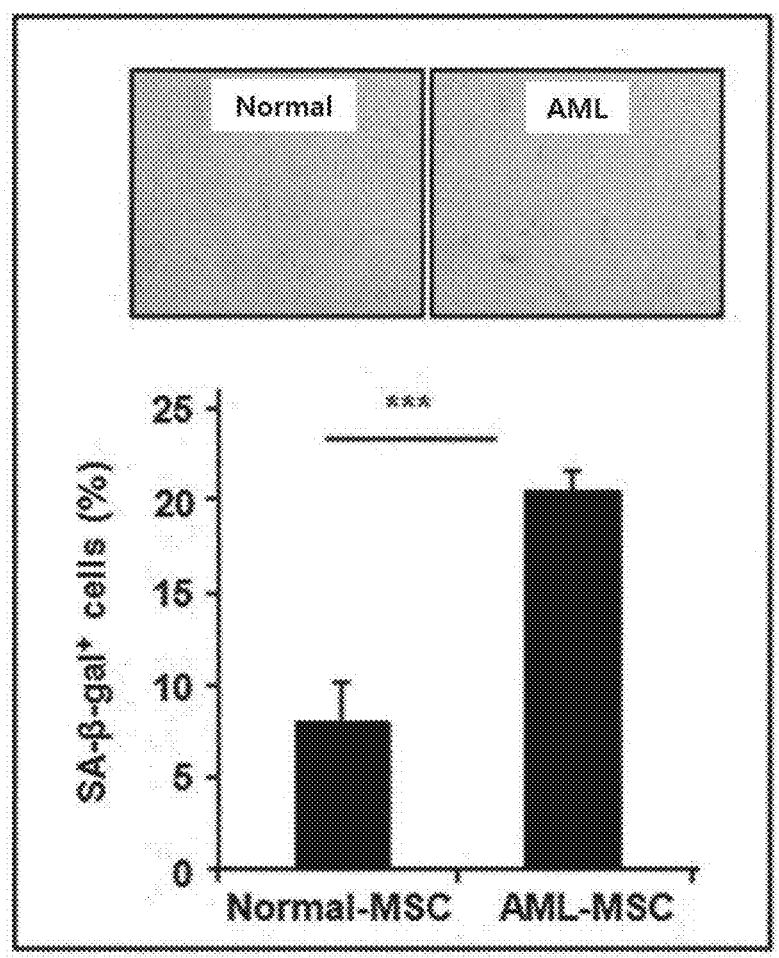
FIG. 1E shows the result comparing the aging-associated beta-galactosidase activity of mesenchymal cells in bone marrows of normal donors and AML patients (three repeated experiments, mean±SEM (standard error of the mean), n=12 for AML, n=9 for normal donors).

For the self-renewal capacity test, the aging-associated β-galactosidase activities of the culture-derived MSCs obtained from three normal donors or four acute myeloid leukemia patients (including M1, M2, M5a, AML/myelodysplastic subtypes) were analyzed (normal; n=9, AML; n=12). By using a kit (Cell Signaling Inc., Denver, Mass., USA), aging-associated β-galactosidase (SA-β-gal) activities were tested in accordance with the manual. Images were shown at the tip of FIG. 1C, and the mean±SEM from the results of three repeated experiments were shown at the bottom. As shown in FIG. 1E, the β-galactosidase activity appeared to be higher in AML-MSC.

Figure 1F:
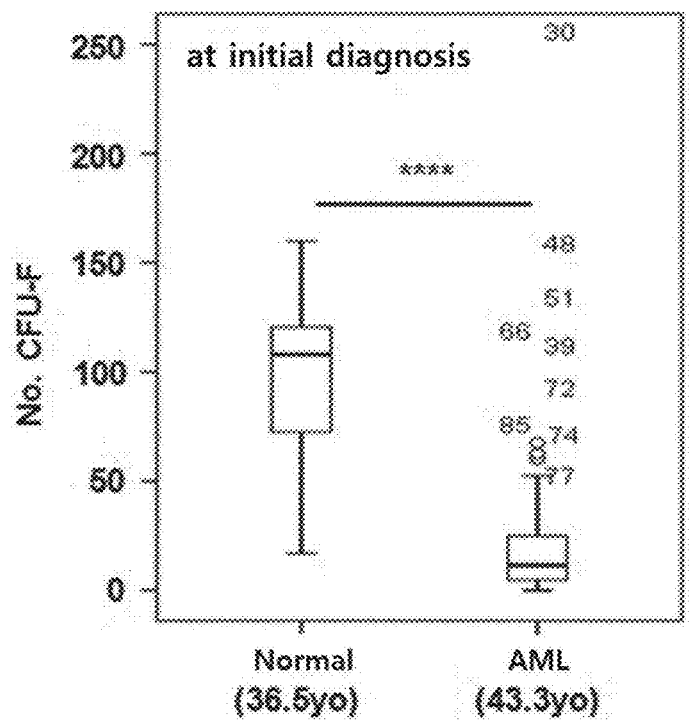
FIG. 1F shows the result comparing the number of CFU-F at the initial diagnosis in bone marrows of normal donors and bone marrows of AML patients of the same age as them. The number in parentheses represents the average age (n=51 for AML, n=11 for normal donors).
Figure 1G:
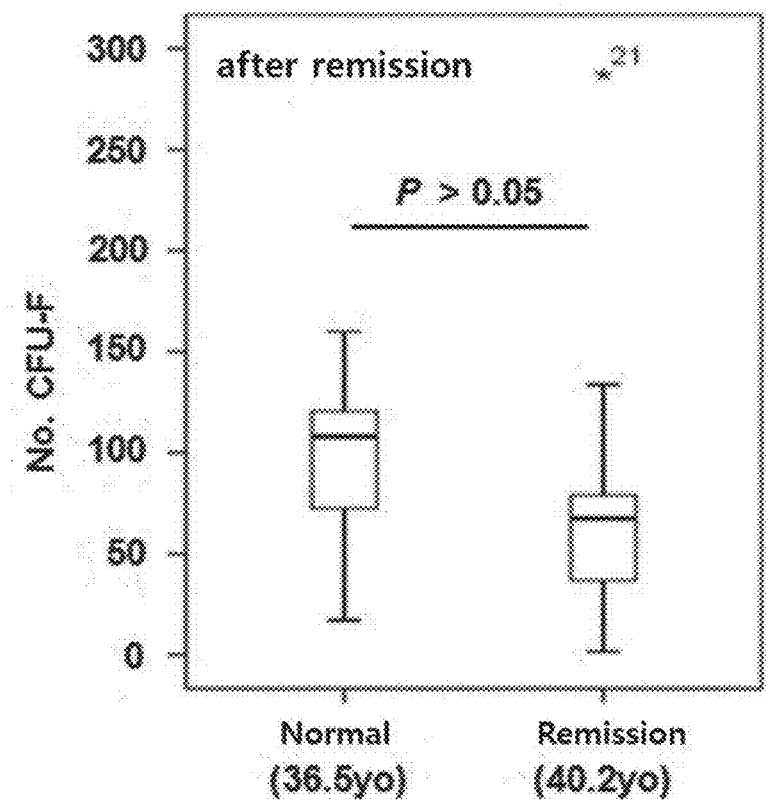
FIG. 1G shows the result comparing the number of CFU-F in bone marrows of AML patients after the complete remission and normal donors (n=17 for the AML remission group, n=11 for normal donors).

Furthermore, to evaluate whether such change of the mesenchymal cells is maintained even after remission of AML, the CFU-F at the initial diagnosis and the CFU-F after remission were compared and analyzed. As a result, although the total number of colony forming cells in the acute myeloid leukemic bone marrow was lower than age-matched normal bone marrows, when the acute myeloid leukemia patients reached the complete remission (CR), this difference was not observed any more (FIG. 1F, FIG. 1G). This means that the change of mesenchyma in the acute myeloid leukemic bone marrow reflects the ongoing leukemogenic activities.

Figure 2A:
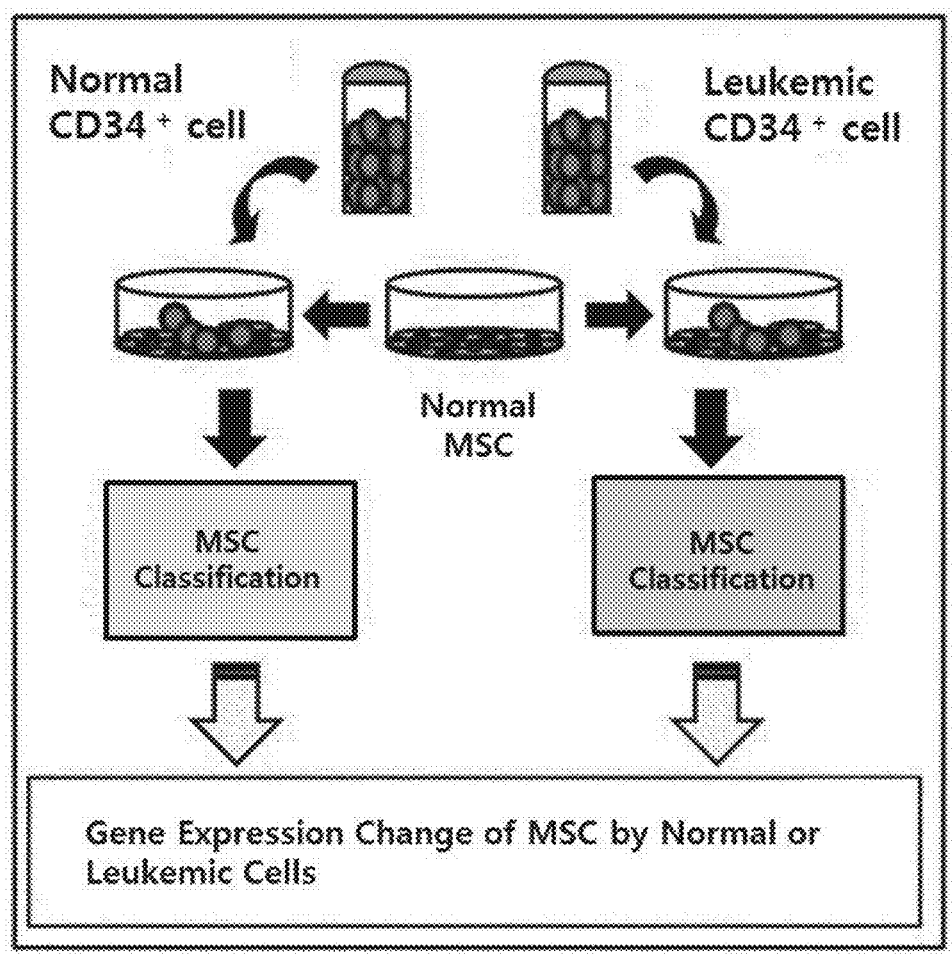
FIG. 2A is a schematic diagram showing the experimental design for the gene expression analysis in MSCs co-cultured with AML blasts or normal hematopoietic stem cells (n=3 per each group).

In order to examine whether the leukemic blasts directly cause changes in mesenchyma confirmed from the results above, the mesenchymal stromal cells were co-cultured with normal CD34$^+$ cells or leukemic CD34$^+$ cells for 5 days and separated and purified from hematopoietic cells to analyze the gene expression of the separated and purified cells. The gene expression in the mesenchymal stromal cells was analyzed by Illumina Bead Chip array hybridization analysis. For six expression profiles, the median absolute deviation (MAD) was calculated and the highly variable genes (that is, the top 1000 genes of the median absolute deviation) were selected for hierarchical clustering having the average linkage. The transfer profiles of the mesenchymal stromal cells co-cultured with leukemic cells were compared with the mesenchymal stromal cells co-cultured with normal hematopoietic progenitors (FIG. 2A).

Figure 2B:
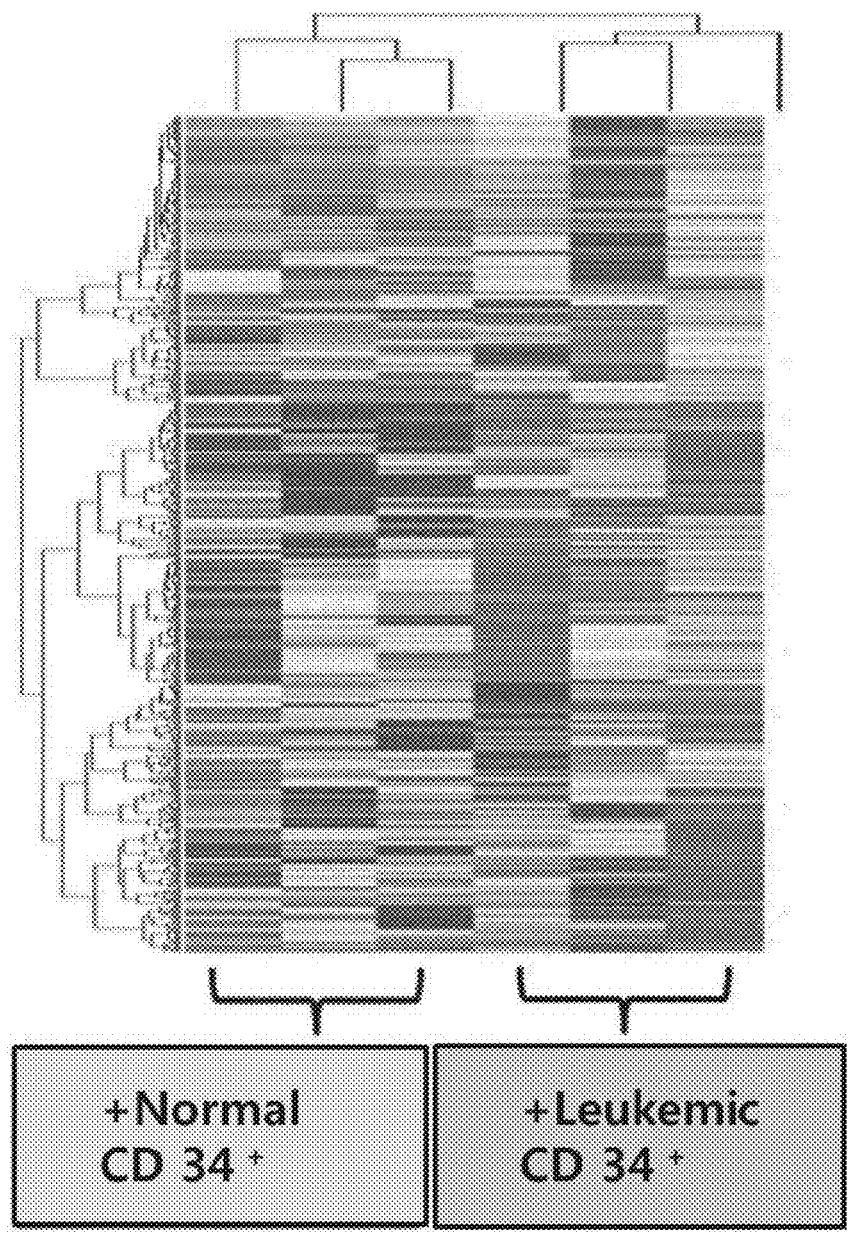
FIG. 2B shows a hierarchical clustering of 1000 various probes (MAD>0.04). A heat map represents relatively upwardly-(red) and downwardly-(blue) controlled parts.

The hierarchical clustering of the very variable genes showed substantial differences in trasciptomes by clearly distinguishing the co-cultured mesenchymal stromal cells from the normal blasts and leukemic blasts (FIG. 2B).

Figure 2D:
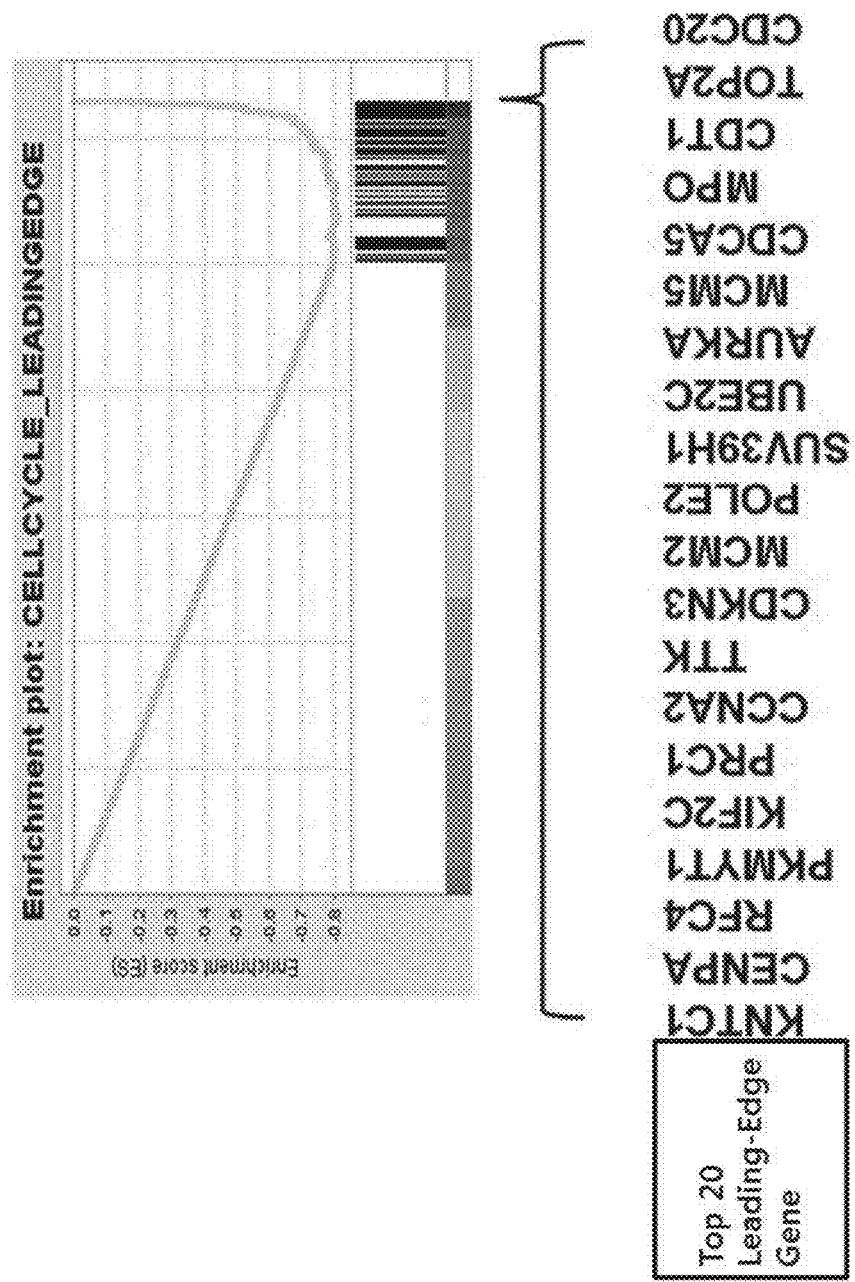
FIG. 2D shows an enrichment plot of 105 'cell cycle'-associated gene sets.
Figure 2E:
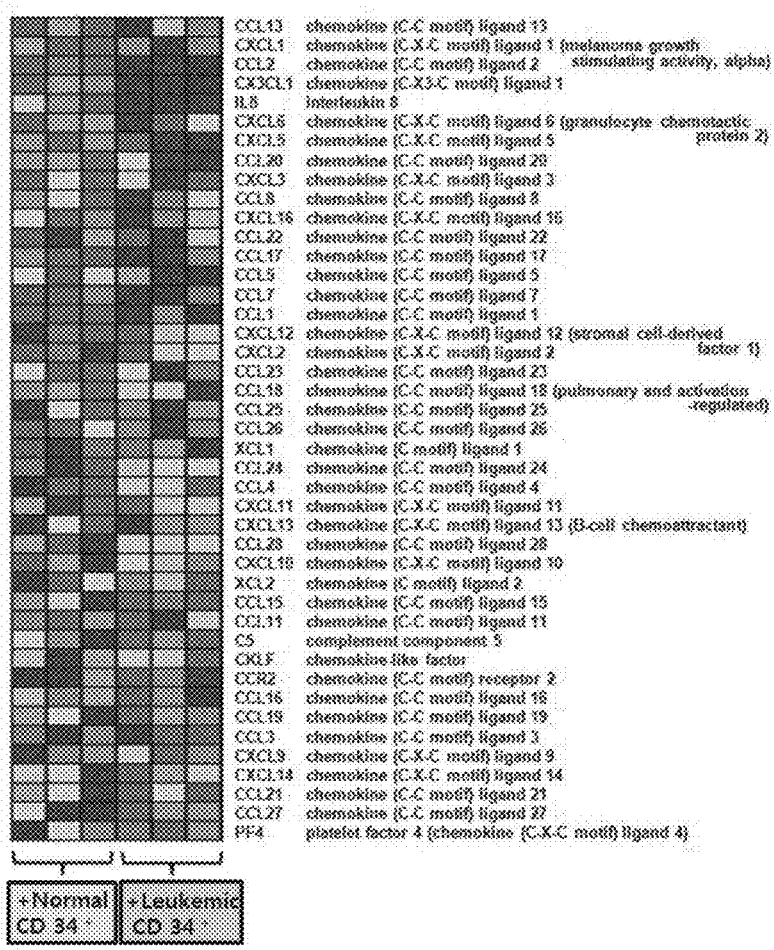
FIG. 2E relates to expression levels of cytokine-associated genes, and shows relative expression levels of 43 genes belonging to 'CHEMOKINE_RECEPTOR_BINDING' GO (the red color represents an upward control and the blue color represents a downward control).

To confirm functions of candidate molecules associated with changes of these transcriptomes, GSEA (Gene Set Enrichment Analysis) was carried out, which analyzes enrichment of gene sets functionally associated from Gene Ontology (GO; MSigDB c5 categories). In 1000 permutations of genes for each GO category a significant normal P value was estimated. The multiple test adjustment was performed to select a significant (FDR <0.1) GO category. Overall, 11 and 80 GO categories in the mesenchymal stromal cells co-cultured with leukemic CD34$^+$ showed a significant (FDR <0.1) enrichment of upwardly- and downwardly-controlled genes (FIG. 2C). Importantly, the significant enrichment of genes for "cell-cycle" and the associated functions thereof (for example, "chromosome," and "DNA cloning") was observed among downwardly-controlled GO categories under leukemia conditions. This is consistent with the loss of proliferation in the mesenchymal stromal cells from acute myeloid leukemia patients. The enrichment plots of 105 'cell cycle'-associated gene sets appeared the top 20 leading edge genes (FIG. 2D and Table 1). In contrast, two cytokine-associated GO functions were observed among the upwardly-controlled GO categories in leukemia-cultured mesenchymal stromal cells ("chemokine receptor binding" and "chemokine activity") (FIG. 2C and FIG. 2E).

These results show that leukemic cells induce the transcriptomic reprogramming obviously different from normal hematopoietic cells with significant inhibition of cell cycle-associated genes and upward control of cytokine-associated genes.

TABLE 1

Top 20 leading edge genes downwardly-controlled
from MSC co-cultured with leukemic cells

| Gene Symbol | Gene Name |
| --- | --- |
| KNTC1 | Kinetochore associate1 |
| CENPA | Centromere protein A |
| RFC4 | Replaication factor C subunit 4 |
| PKMYT1 | Protein kinase, membrane associated tyrosine/threonine 1 |
| KIF2C | Kinesin family member 2C |
| PRC1 | Protein regulator of cytokinesis 1 |
| CCNA2 | Cyclin A2 |
| TTK | Dual specificity protein kinase TTK |
| CDKN3 | Cyclin-dependent kinase inhibitor 3 |
| MCM2 | Minichromosome maintenance complex component 2 |
| POLE2 | Polymerase (DNA directed), epilon 2, accessory subunit |
| SUV39H1 | Suppressor of variegation 3-9 homolog 1 (*Drosophila*) |
| UBE2C | Ubiquitin-conjugating enzyme E2C |
| AURKA | Aurora kinase A |
| MCM5 | Minichromosome maintenance complex component 5 |
| CDCA5 | Cell division cycle associated 5 |
| MPO | Myeloperoxidase |
| CDT1 | Chromatin licensing and DNA replication factor 1 |
| TOP2A | Topoisomerase (DNA) II alpha 170 kDa |
| CDC20 | Cell division cycle 20 |

EXAMPLE 2

Figure 3A:
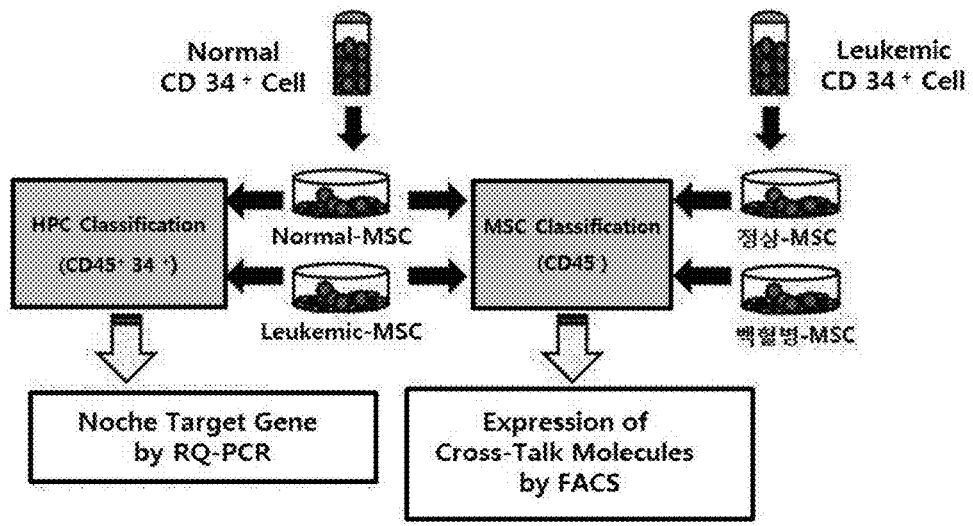
FIG. 3A is a schematic diagram of the experiment analyzing the expression change of cross-talk molecules.

Resetting of cross-talk in microenvironment for normal cells and leukemic Cells of Leukemic Niches To investigate the changes of leukemia-derived mesenchymal stromal cells, the expression change of cross-talk molecules in the mesenchymal stromal cells was tested. The mesenchymal expression of cross-talk molecules, jagged-1 and CXCL-12(+), stimulating HSC self-renewal in niches during co-culture with normal cells and leukemic cells was examined (FIG. 3A).

For the analysis of the fresh bone marrow stromal cells, bone marrow mononuclear cells were stained with specific antibodies for subsets of mesenchymal cells and endothelial cells, and analyzed by a flow cytometer. The flow cytometric analysis of jagged-1 or CXCL-12 expression in fresh mesenchymal stromal cells was carried out by staining into a goat anti-jagged-1 antibody (Sigma-Aldrich, St. Louis, Md., USA) or intracellular staining into a mouse anti-CXCL12/SDF-1 antibody (R & D System, Minneapolis, Minn., USA). For the cultured mesenchymal stromal cells, the jagged-1 was detected by intracellular staining into rabbit anti-jag-ged-1 antibody (Cell Signaling Inc.). For immunohistochemistry, bone marrow sections were deparaffinized, and immunohistochemical staining was performed by using SPlink HRP Detection Bulk Kit (Golden Bridge International Inc., Mukilteo, Wash., USA). The jagged-1 and CXCL-12 in the bone marrow sections were detected with the rabbit anti-jagged-1 antibody (Cell Staining Co.) or the mouse anti-CXCL12/SDF-1 antibody (R & D System) detecting intracellular domain of each molecule. Sections were visualized by counterstain into 3,3'-diaminobenzidine substrate and hematoxylin.

Figure 3B:
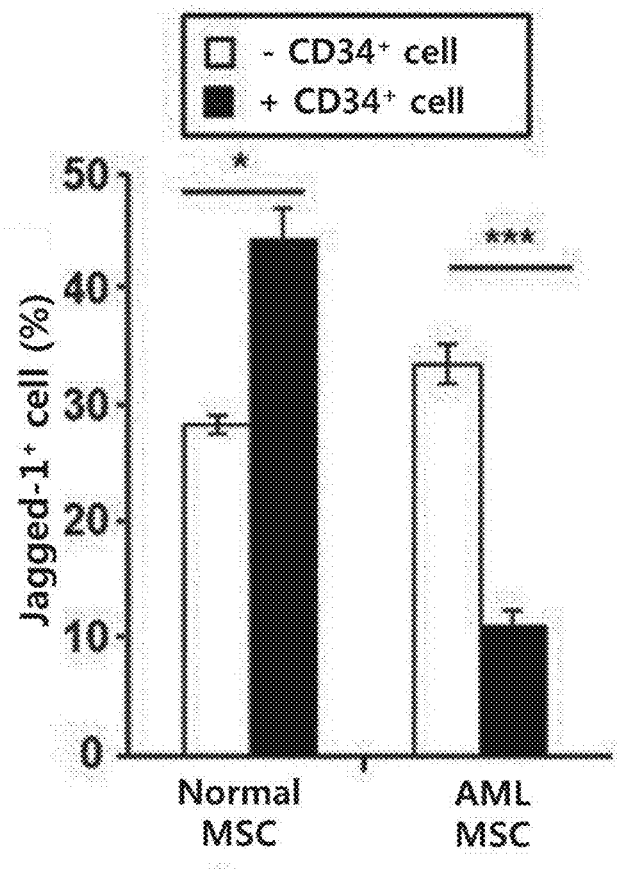
FIG. 3B shows the result analyzing the expression of jagged-1 or CXCL-12 protein in normal and AML-MSCs (M2, M5a) in the presence or absence of normal $CD34^+$ cells (four repeated experiments, n=4 per each group, *; $p<0.05$, ***; $p<0.001$).
Figure 3D:
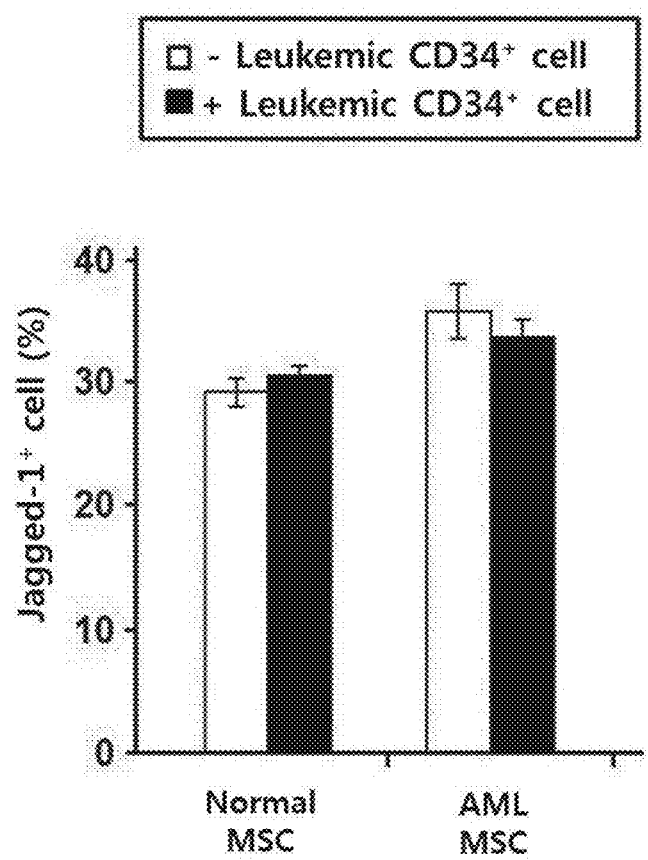
FIG. 3D shows the expression percentage of jagged-1 in the cultured normal or AML-MSCs (M2, M5a) in the presence or absence of leukemic blasts (mean±SEM, three repeated experiments, n=3 per each group).
Figure 3E:
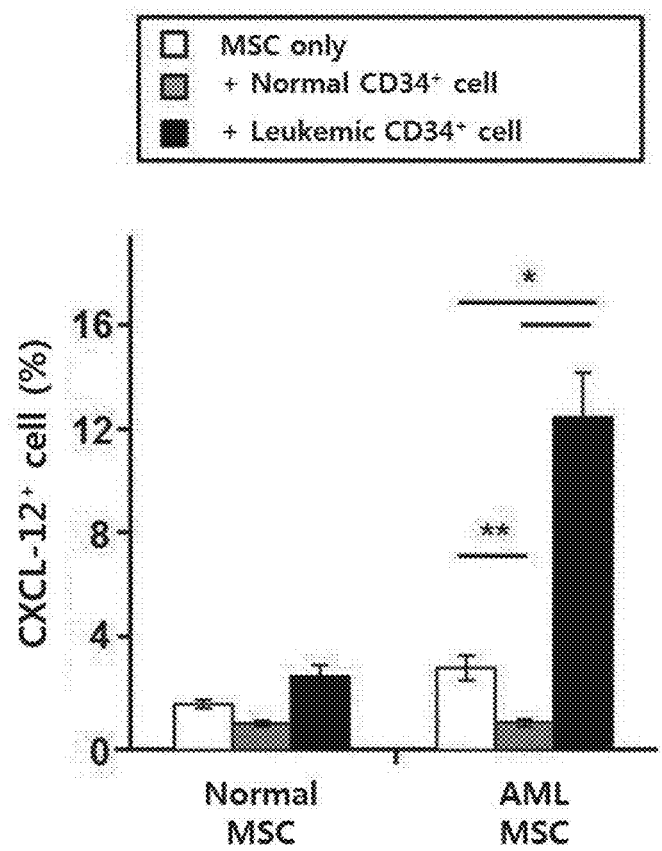
FIG. 3E shows the result analyzing the expression change of CXCL-12 in normal MSCs by co-culture with normal or leukemic blasts using a flow cytometer. This shows the average percent of CXCL-12(+) cells in each group of MSCs (+) with the SEM (three repeated experiments, n=3 per each group).

As a result, the normal mesenchymal stromal cells showed a sharp increase of jagged-1(+) cells in response to co-culture with normal hematopoietic progenitors, while the acute myeloid leukemia-mesenchymal stromal cells further decreased it and showed the apparent reaction of the acute myeloid leukemia-mesenchymal stromal cells in the opposite direction (FIG. 3B). Thus, the normal hematopoietic progenitors co-cultured with the acute myeloid leukemia-mesenchymal stromal cells showed a significant inhibition of down-stream notch signals, Hes-1 or Hes-5 over co-culture with normal mesenchymal stromal cells (FIG. 3C). In contrast, during co-culture with leukemia blasts, the jagged-1(+) cells did not increase in the normal mesenchymal stromal cells, and also the reduction of the acute myeloid leukemia-mesenchymal stromal cells was not observed (FIG. 3D), and thus it showed that leukemic blasts and normal hematopoietic progenitors involved separate cross-talk under the leukemic microenvironment. Similarly, during co-culture with normal cells or leukemic cells, when testing about the change of mesenchymal stromal cells in CXCL-12(+) cells, the acute myeloid leukemia-mesenchymal stromal cells showed optionally the apparent increase of CXCL-12(+) cells in response of the leukemic cells, while it decreased during co-culture of normal hematopoietic cells (FIG. 3E).

Figure 3F:
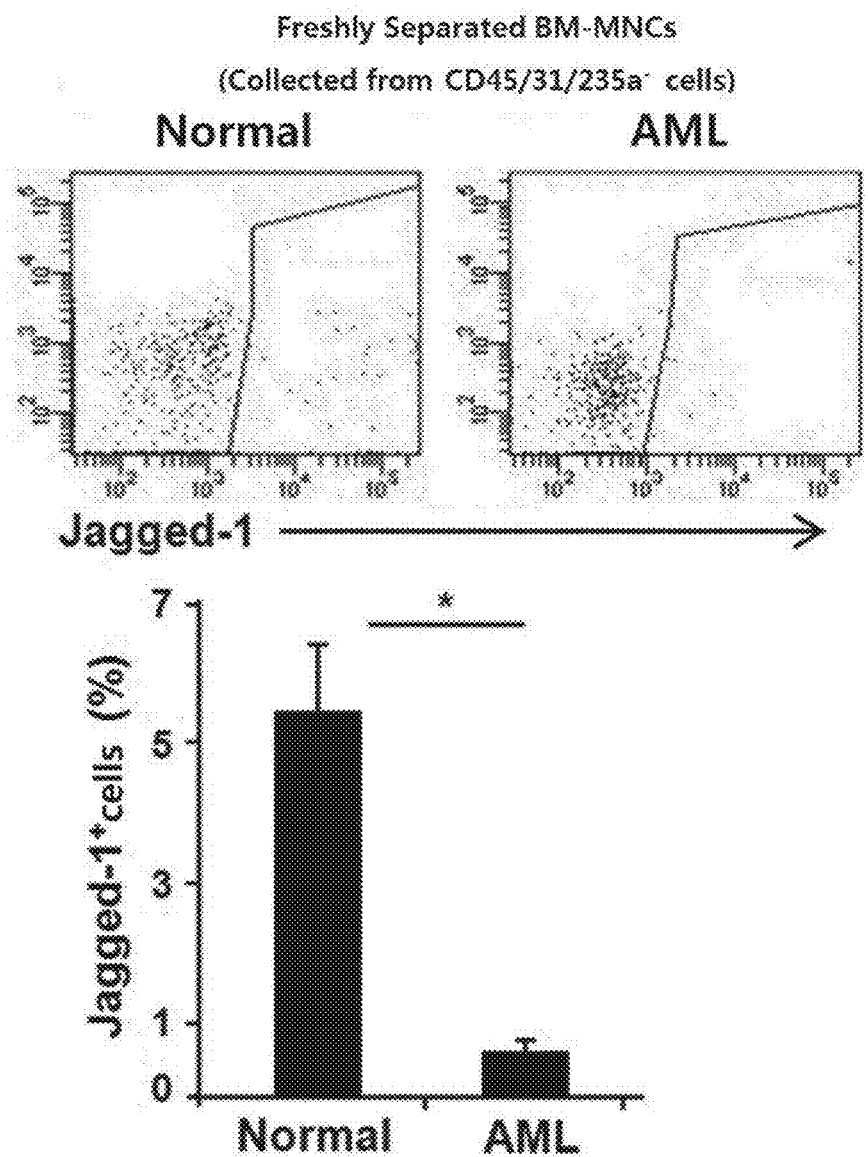
FIGS. 3F and 3G show the in-vivo expression degrees of jagged-1 (FIG. 3F) and CXCL-12 (FIG. 3G) in fresh BMs of normal donors and AML patients (the average % of jagged-1 (+) or CXCL-12 (+) cells among MSCs (CD45−31−235a−), n=8 for the normal donor group, n=46 for AML).
Figure 3G:
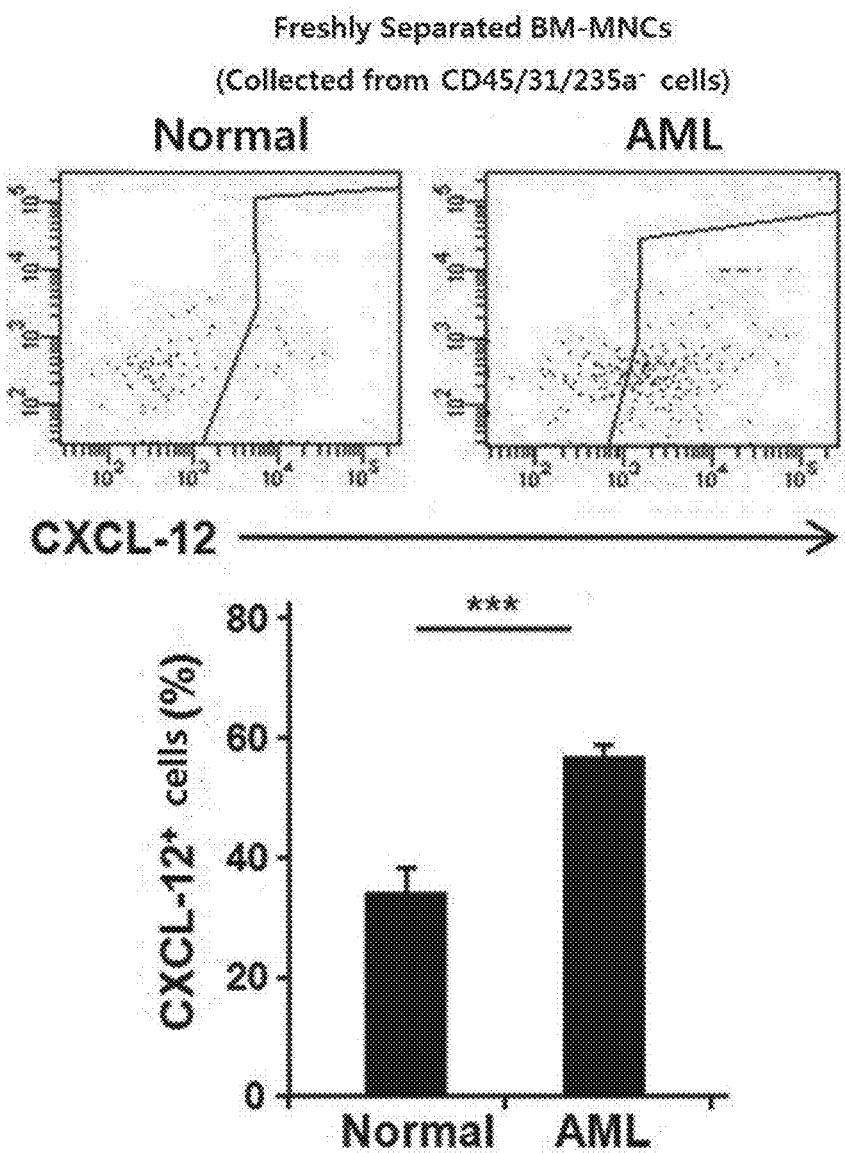

To further explore these findings under in vivo leukemic conditions, BMs of the AML patients were screened for cross-talk molecules in fresh, non-cultured mesenchymal stromal cells. The AML BMs showed the apparent decrease in % of jagged-1(+) cells among the mesenchymal stromal cells over the normal bone marrow (5.4±1.0 vs. 0.5 ±0.2% for normal and acute myeloid leukemia, respectively) (FIG. 3F). Similarly, the CXCL-12(+) cells among the mesenchymal stromal cells significantly increased in the acute myeloid leukemic bone marrows over the normal marrows (42.0±5.2 versus 69.9±2.8% for normal and acute myeloid leukemia, respectively) (FIG. 3G), so that the changes of cross-talks observed from the in vitro model were reproduced. Interestingly, these changes observed at the initial diagnosis, that is, the decrease of jagged-1(+) or the increase of CXCL-12(+) mesenchymal stromal cells, were reversed if the analysis was performed after the bone marrows of the same patients reached the complete remission (FIG. 3H). This means that leukemia cells cause the remodeling of niche cross-talk as an inherent part of progression leukemia.

EXAMPLE 3

Functional impact of altered microenvironment to normal HSC

The impact of the altered microenvironment of mesenchymal stromal cells in AML on the function of the HSC was evaluated. To this end, the mesenchymal stromal cells were co-cultured with normal or acute myeloid leukemia-mesenchymal stromal cells to analyze the impact that the leukemic mesenchymal stromal cells affect normal hematopoietic function or leukemic function.

The mesenchymal stromal cells were irradiated (1500 cGy) 24 hours before co-culture. And the mesenchymal stromal cells were co-cultured with normal or leukemic CD34$^+$ cells for 5 days in a long-term culture-initiating cell media (LTC-IC media; Stem Cell Technology Inc., Vancouver, Canada, H5100) in the presence of a cytokine mixture consisting of 100 ng/ml human SCF, 100 ng/ml human Flt3L and 20 ng/ml human 1L-3, IL-6, and G-CSF (ProSpec-TanyTechnoGene Ltd, Rehovot, Israel).

The normal CD34$^+$ cells from cord blood were co-cultured on MSCs derived from 2 normal donors under stroma-free conditions (SF) or cultured under leukemic MSCs conditions derived from 4 AML patients for 5 days to analyze the total increased amount of CD34$^+$ cells (three repeated experiments, n=7 per each group) (*; p<0.05).

As a result, as shown in FIG. 4A, the significant in vitro increase of CD34$^+$ cells was observed in the case of co-culturing on normal MSCs, but this increase was not observed in the case of co-culturing on AML-MSCs.

The normal CD34$^+$ cells co-cultured on MSCs of each group were transplanted in the irradiated (250 rad) NSG mice (1X10$^4$ CD34$^+$ cells/mouse). 8 weeks after transplantation, the BM cells were analyzed to examine the presence or absence of engraftment of the human hematopoietic cells (hCD45$^+$). NOD/SCID-γnull (NSG) mice were purchased from Jackson Laboratory (Bar Harbor, Me., USA) and kept in a filtered individual ventilation cage. For a repopulating analysis, the mice (7 to 10 weeks of age) were irradiated (250 cGy), and hematopoietic cells were injected intravenously. 8 weeks after transplantation, human cell engraftment was analyzed by staining with a flow cytometer.

Figure 4B:
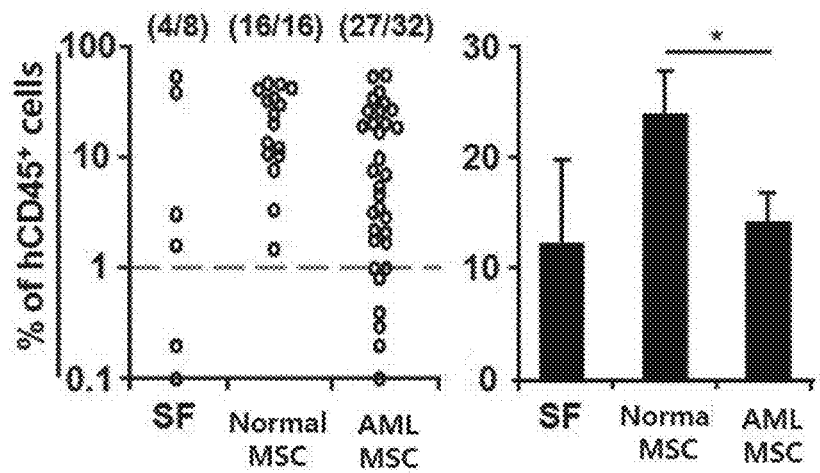
FIG. 4B shows the result analyzing engraftment of BM cells to human hematopoietic cells (hCD45+) after transplanting normal CD34+ cells co-cultured with MSCs of each group to the irradiated (250 rad) NSG mice (1X10$^4$ CD34+ cells/mouse).

As a result, in the left graph of FIG. 4B, the numbers of mice showing a positive response (higher than 1%) of the total tested mice were represented in parentheses. The average human cell engraftment levels in normal and leukemic MSC groups were represented in the right side of FIG. 4B (* p<0.05). As a result, when transplanted into NSG mice, the normal hematopoietic progenitors co-cultured on AML-MSCs showed repopulating activities having a low level over the cells cultured on normal MSCs (FIG. 4B).

Figure 4C:
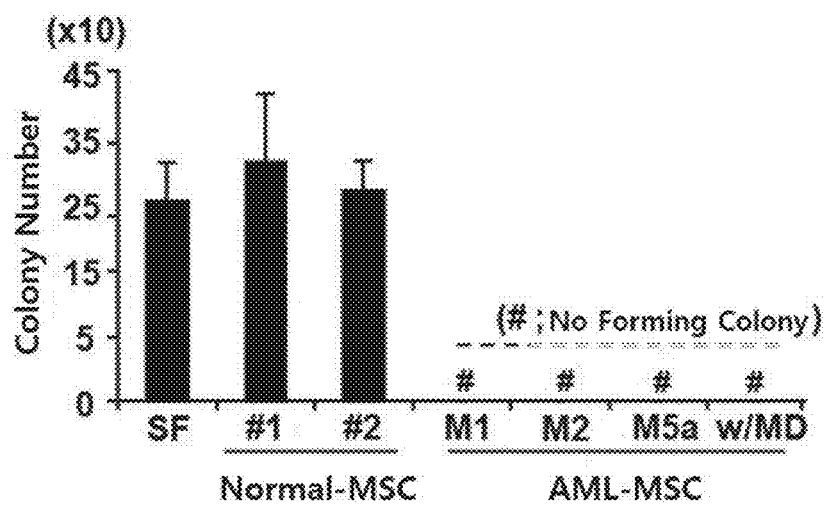
FIG. 4C shows the result analyzing LTC-ICs in normal and AML-MSCs (after long-term culture, number of 400 CD34$^+$ cell-derived colonies, four repeated experiments, n=4 per each group).

For analysis on maintenance of primitive hematopoietic cell populations by long-term culture-initiating cell (LTC-IC) assay, normal CD34$^+$ cells co-cultured with each of the MSCs were long-term cultured for 6 weeks, and then plated on semi-solid media for forming the colony. After the long-term culture, as the number of colonies derived from 400 input CD34$^+$ was analyzed (four experiments, n=4 per each group), an enormous loss of the long-term culture-initiating cells appeared in the CD34$^+$ cells co-cultured on AML-MSCs (FIG. 4C). On the other hand, the loss did not appear in the normal MSCs group. This means that the AML-MSCs exert an inhibitory effect on normal hematopoiesis action and primitive hematopoietic cells are outstandingly affected by the adverse effect of the leukemic mesenchymal stromal cells.

The AML blasts (M1, M3, HL-60) were cultured under stroma-free conditions (SF) or co-cultured with normal or AML-MSCs (M2, M5a) for 3 days to analyze the numbers of the leukemic cells (CD45$^+$) (three experiments, n=5-6 per each group). In addition, the leukemic cells co-cultured with MSCs of each group were transplanted in the irradiated NSG mice. 6 weeks after transplantation, in the peripheral blood (PB) and BMs, the engraftment of the leukemic cells (hCD45 +) was analyzed (n=6 per each group).

Figure 4D:
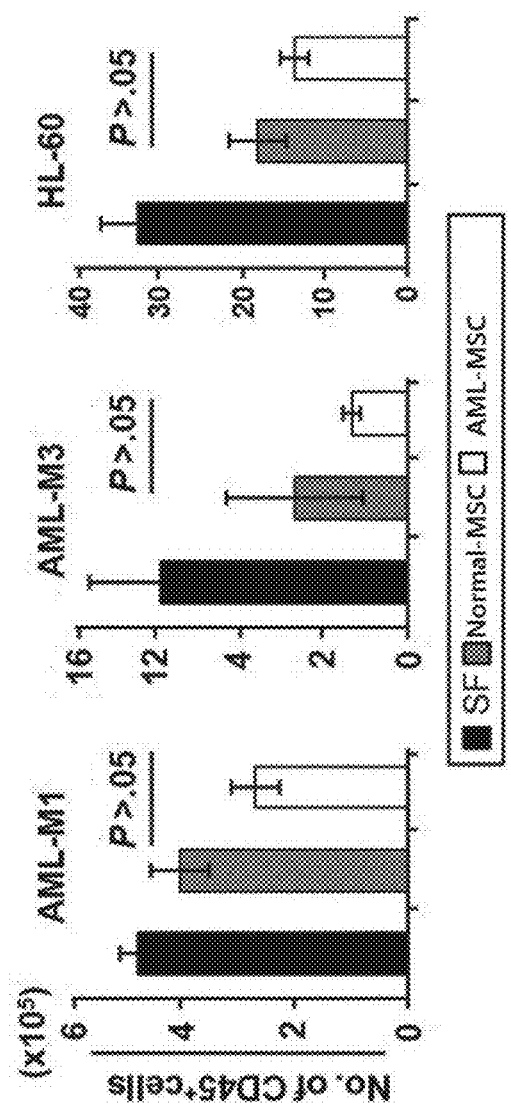
FIG. 4D shows the effect on leukemic cell proliferation of normal or AML-MSCs (mean±SEM, three repeated experiments, n=5-6 per each group).
Figure 4E:
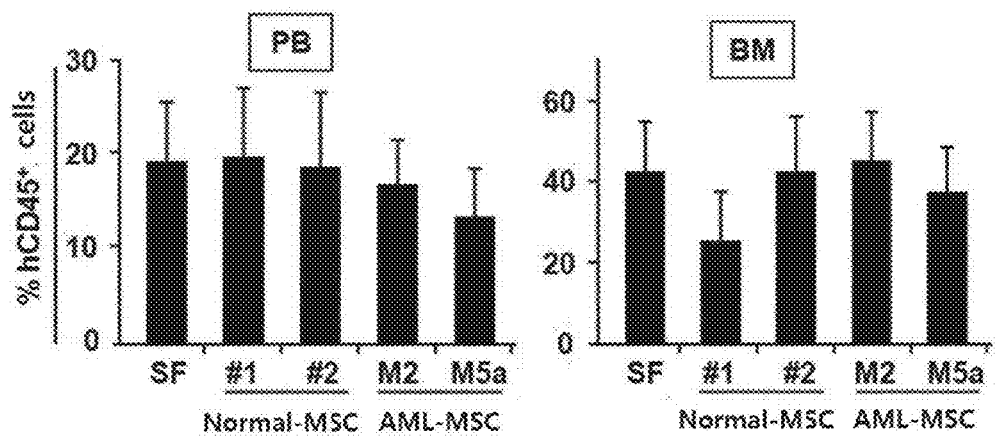
FIG. 4E shows the result analyzing engraftment (hCD45+) of leukemic cells in peripheral blood (PB) and BMs after transplanting leukemic cells (HL-60) co-cultured with MSCs of each group to the irradiated NSG mice (average engraftment% (SEM), n=6 per each group).

As a result, unlike the long-term culture-initiating cell assay, no difference appeared in the in vitro proliferation or the in vivo leukemogenesis (FIG. 4D, FIG. 4E). This suggests that the leukemic cells have a resistance to the adverse effect of the leukemic niches.

In addition, the cell cycle of the leukemic cells (HL-60) co-cultured with MSCs of ach group was analyzed by staining with fluorescence and pyronin (Hoescht and pyronin), and the % cell populations of the $G_0$ phase were analyzed (two experiments, SF; n=2, the co-cultured group; n=5-6).

The leukemic cells (HL-60) was treated with Ara-C (2 μM) during co-culturing with MSCs of each group for 2 days, and among the leukemic cells (CD45$^+$), the cells in the process of apoptosis (AnnexinV+PI−) were analyzed by a flow cytometer (three experiments, SF; n=3, the co-cultured group; n=5-6).

Figure 4F:
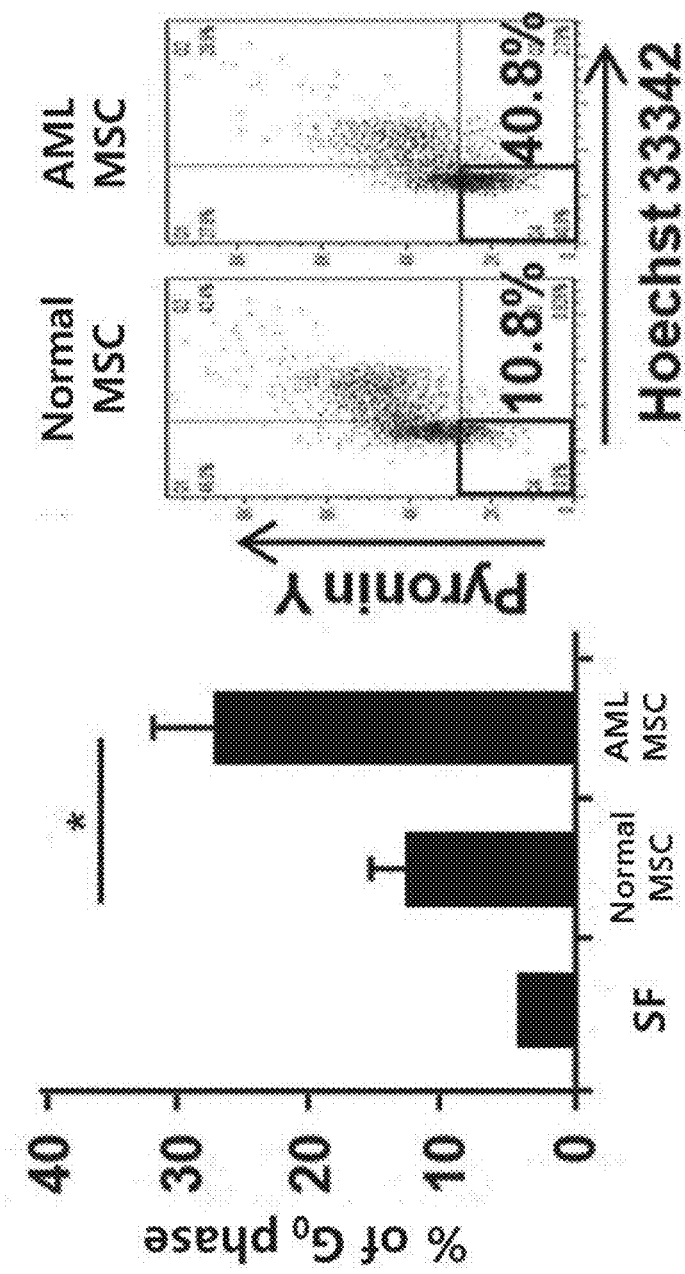
FIG. 4F shows the result analyzing % of the cell population in $G_0$ phase by fluorescence/pyronin Y (Hoescht/Pyronin) staining from cell cycles of leukemic cells (HL-60) co-cultured with MSCs of each group (mean SEM, twice repeated experiments, n=2 for SF, n=5-6 for the co-cultured group, *p<0.05).
Figure 4G:
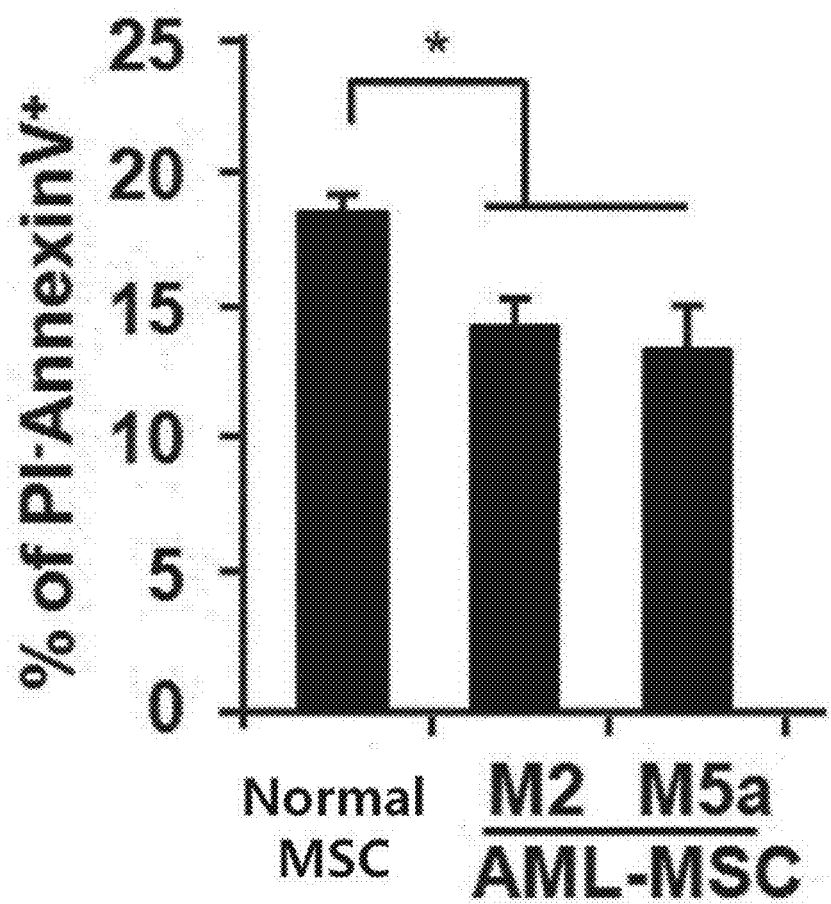
FIG. 4G shows the result analyzing cells in the apoptosis process of Ara-C (2 μM) treated leukemic cells (HL-60) by a flow cytometer during the co-culture (mean±SEM, three repeated experiment, n=3 for SF, n=5-6 for the co-cultured group).

As a result, the co-culture into the acute myeloid leukemia-mesenchymal stromal cells led to the arrest state the leukemic cells in a ratio higher than the co-culture into the normal mesenchymal stromal cells, and gave a higher resistance to apoptosis derived by the Ara-C treatment (FIG. 4F, FIG. 4G). At the same time, these results suggest that the leukemic microenvironment selectively inhibits normal hematopoietic cells, but exerts the marked effect on normal cells and leukemic cells in such a way to support the leukemic activity and the chemo-resistance of leukemic cells.

EXAMPLE 4

Remodeling of niche as a prognostic parameter in leukemia patients

The functional effects of the stromal remodeling for normal hematopoiesis action and leukemogenic activities were found, and then, the hypothesis that the difference in such stromal remodeling may contribute to heterogeneity in the clinical courses of acute myeloid leukemia patients was built up. To test that possibility, a cohort study was designed, which investigates the correlation between the bone marrow stroma changes at the initial diagnosis of acute myeloid leukemia and their subsequent clinical courses for 5 to 8 years after remission. For the cohort study, the primitive bone marrow samples of acute myeloid leukemia patients having the full tracking data for 5 to 8 years after remission were collected (Table 2). The stromal cell compositions were tested for the acute myeloid leukemia patient group maintaining the complete remission for 5 to 8 years after remission (CR, n=29), the acute myeloid leukemia patient group relapsed after that (relapse; R; n=14) and the acute myeloid leukemia patient group representing the obstinate reaction against chemotherapy (refractory; Rf; n=5) together with BMs from normal donors (Nr; n=12).

TABLE 2

List of AML Patients Selected from Cohort Study

| No. | Gender | Age | Type | Prognosis |
| --- | --- | --- | --- | --- |
| #1 | F | 48 | M0 | CR |
| #2 | F | 65 | M0 | CR |
| #3 | F | 23 | M1 | CR |
| #4 | M | 38 | M1 | CR |
| #5 | M | 43 | M1 | CR |
| #6 | F | 50 | M1 | CR |
| #7 | F | 20 | M1 | CR |

TABLE 2-continued

List of AML Patients Selected from Cohort Study

| No. | Gender | Age | Type | Prognosis |
|---|---|---|---|---|
| #8 | M | 36 | M1 | CR |
| #9 | F | 47 | M1 | CR |
| #10 | F | 52 | M1 | CR |
| #11 | F | 17 | M2 | CR |
| #12 | M | 51 | M2 | CR |
| #13 | F | 23 | M2 | CR |
| #14 | M | 43 | M2 | CR |
| #15 | M | 35 | M2 | CR |
| #16 | M | 33 | M2 | CR |
| #17 | M | 34 | M2 | CR |
| #18 | M | 29 | M2 | CR |
| #19 | F | 18 | M2 | CR |
| #20 | F | 32 | M2 | CR |
| #21 | M | 56 | M2 | CR |
| #22 | F | 60 | M2 | CR |
| #23 | M | 37 | M3 | CR |
| #24 | M | 42 | M3 | CR |
| #25 | M | 39 | M3 | CR |
| #26 | M | 19 | M3 | CR |
| #27 | F | 40 | M3 | CR |
| #28 | M | 68 | M3 | CR |
| #29 | M | 20 | M4 | CR |
| #30 | F | 48 | M1 | Relapse |
| #31 | M | 62 | M1 | Relapse |
| #32 | M | 57 | M1 | Relapse |
| #33 | F | 48 | M1 | Relapse |
| #34 | F | 16 | M1 | Relapse |
| #35 | M | 35 | M2 | Relapse |
| #36 | M | 36 | M2 | Relapse |
| #37 | F | 42 | M2 | Relapse |
| #38 | F | 48 | M2 | Relapse |
| #39 | F | 17 | M2 | Relapse |
| #40 | M | 51 | M4 | Relapse |
| #41 | F | 21 | M5 | Relapse |
| #42 | M | 38 | M5a | Relapse |
| #43 | M | 52 | M5b | Relapse |
| #44 | M | 55 | M1 | Obstinate |
| #45 | M | 68 | M2 | Obstinate |
| #46 | F | 39 | M4 | Obstinate |
| #47 | M | 56 | M5 | Obstinate |
| #48 | M | 36 | MLD | Obstinate |

Figure 5A:
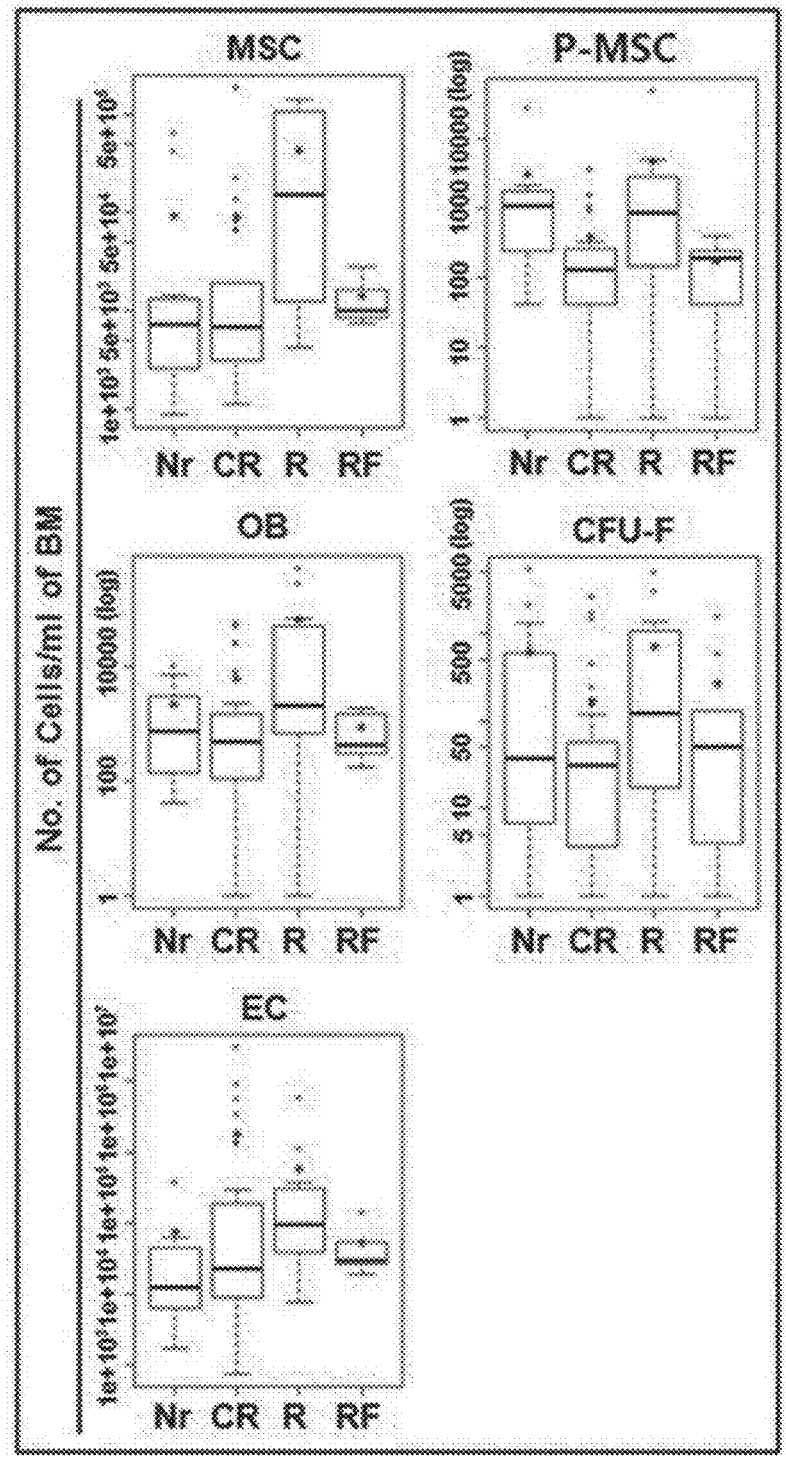
FIG. 5A shows the numbers of MSCs (CD45−31−235a−), endothelial cells (CD45−31−235a−31+) (EC), MSC progenitors (CD45−31−235a−146+166−) (M-progenitors), mature osteoblastic cells (CD146+31−235a−146−166+) (OB), and CFU-Fs contained in 1 ml of the fresh BM.

Although the excessive heterogeneity was observed in the acute myeloid leukemia patients, significant differences were found in stromal components of the bone marrows. That is, the primitive mesenchymal stromal cells in the bone marrow (CD45−31−235a−146+166−; P-MSCs) and the colony forming cells were lower than the normal bone marrows completely remitted, while the differentiated mesenchymal stromal cells (MSCs; CD45−31−235a−) and the osteoblastic cells (CD146+31−235a−146−166+; OB) in the relapse group were higher than in the complete remission group (FIG. 5A). However, among the patient groups there was no significant difference in the content of endothelial cells (EC; CD45−31−235a−31+).

Thus, for prediction of relapses of the remitted acute myeloid leukemia patients, it was determined to evaluate whether these differences in the stromal patterns may be used to identify high-risk patients. To this end, the ROC (receiver operating characteristic) curve and the area under the curve (AUC) measured by the same were applied to analyze predictability of relapses for each stromal component.

As a result, as shown in FIG. 5B, the AUC values for predicting the entire relapse groups by the differentiated mesenchymal stromal cells (0.78±0.07), the primitive mesenchymal stromal cells (0.72±0.09) or the osteoblastic cells (0.7±0.09) were higher than the EC (0.63±0.09), colony forming cells (0.68±0.09) (FIG. 5B). Importantly, the prediction for relapses was more significant when the early relapse (within 1 year; n=10) and the late relapse (more than 1 year; n=4) were separately analyzed. The high number of the primitive mesenchymal stromal cells showed high predictability of the early relapse (within 1 year) (AUC=0.8±0.08) (FIGS. 5B and 5D), which was much more significant for relapse within six months after remission (AUC=0.88±0.06) (FIG. 5C).

Figure 5C:
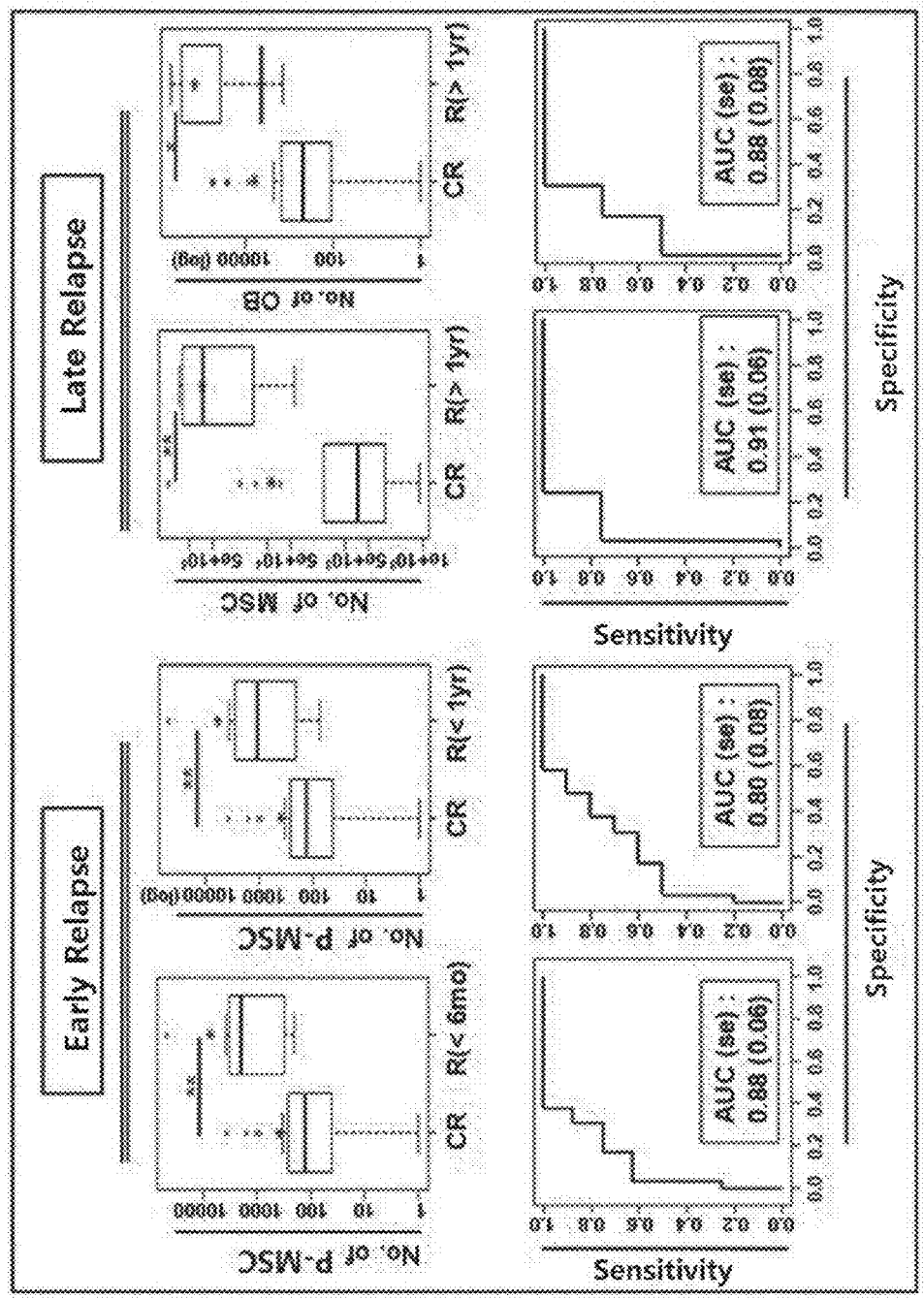
FIG. 5C shows at the top the numbers of biomarkers, which are derived from FIG. 5B, in BM of CR and various relapse groups (95% confidence interval (C.I.). Their ROC (Receiver operating characteristic) curves and AUC values (SE) are shown at the bottom.
Figure 5D:
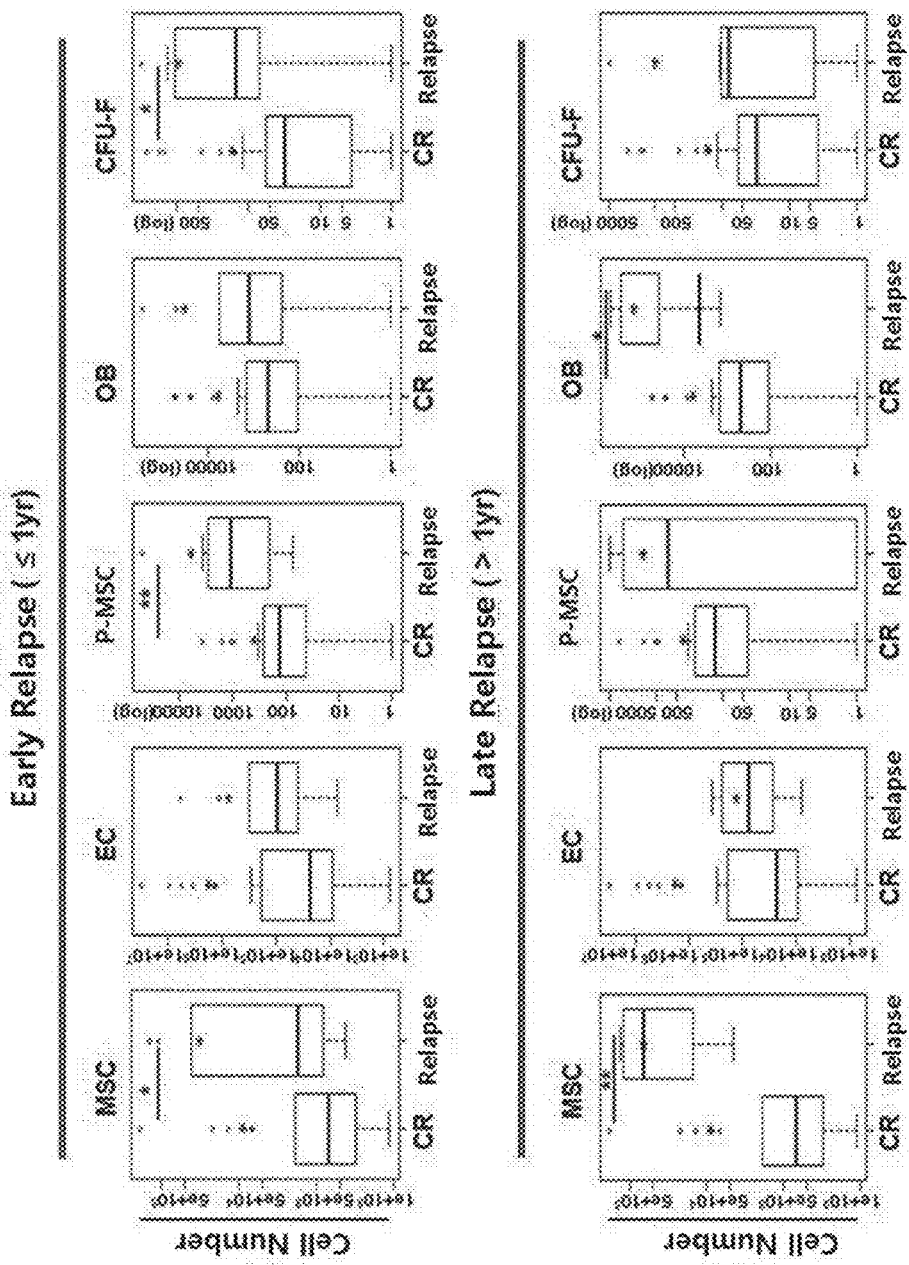
FIG. 5D shows the difference of the BM stromal cell composition according to BM of the CR and relapse AML patients. The numbers of each stromal composition in early relapse (≤1 year) and late relapse (>1 year) groups were represented as compared to the CR group (95% C.I.).

In contrast, remarkable differences appeared about the late relapsed patients (more than 1 year), that is, the significantly high numbers of the mesenchymal stromal cells or osteoblastic cells differentiated in the late relapse group were observed over the complete remission having high predictability (AUC=0.91±0.06 for each differentiated mesenchymal stromal cell, AUC=0.88±0.08 for osteoblastic cells) (FIG. 5C).

Figure 6:
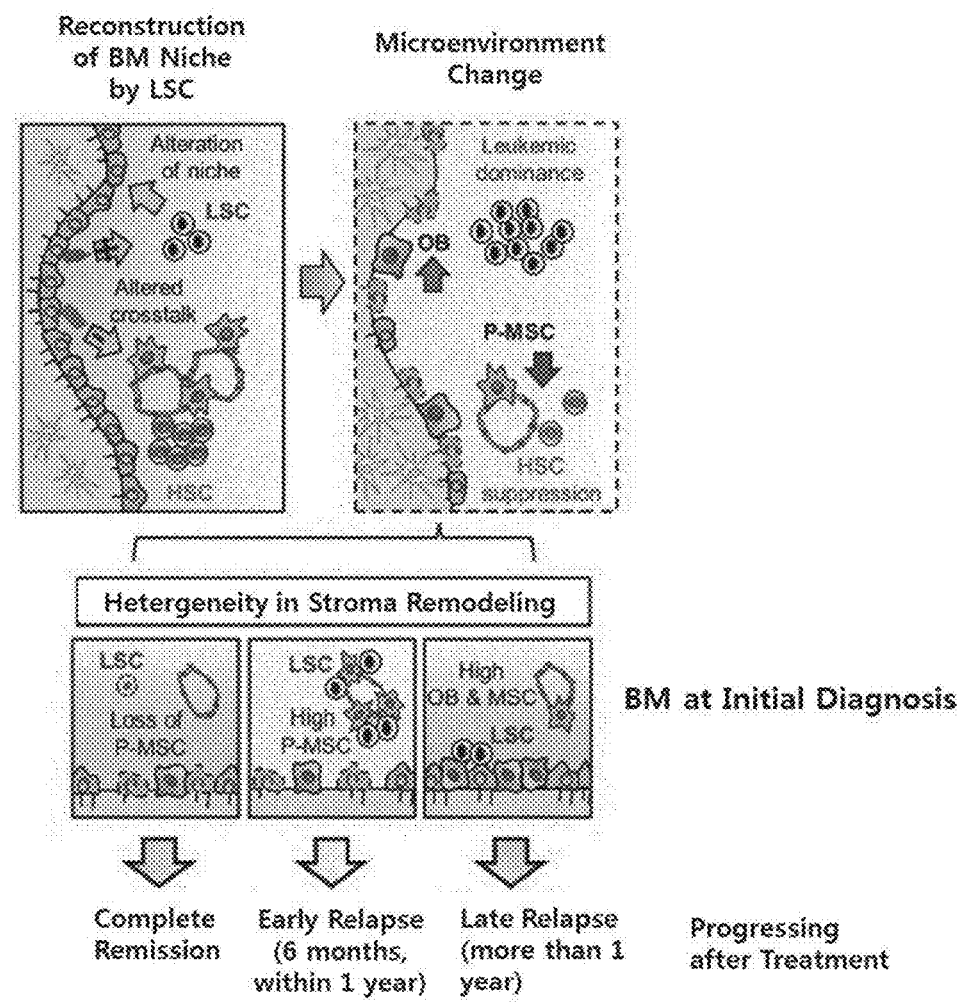
FIG. 6 is a schematic diagram representing changes of leukemia-derived niches and their clinical significance.

These results were combined and shown as a schematic diagram in FIG. 6. In summary, the high number of primitive mesenchymal stromal cells in the bone marrow is highly associated with the early relapse, while the high number of the differentiated mesenchymal stromal cells or osteoblastic cells is associated with the late relapse. That is, the early and late relapses of acute myeloid leukemia are clearly associated with the microenvironment of the stroma (FIG. 6).

Therefore, it suggests that the parameter for heterogeneity in the clinical course of acute myeloid leukemia may function as a potential biomarker for prediction of the clinical course of acute myeloid leukemia patients, and the stroma change in the bone marrow of acute myeloid leukemia patients at the early diagnosis can be a parameter for heterogeneity in the clinical course of such acute myeloid leukemia.

What is claimed is:

1. A method for selecting treatment for an acute myeliod leukemia (AML) patient, comprising:
    i) obtaining a bone marrow sample from said leukemia patient following complete remission from acute myeloid leukemia;
    ii) assaying cells of said bone marrow sample to determine levels of stromal cells selected from the group consisting of primitive mesenchymal stromal cells, differentiated mesenchymal stromal cells and osteoblastic cells;
    iii) referring patients having increased levels of primitive mesenchymal stromal cells in said sample compared to levels of primitive mesenchymal stromal cells of a healthy, leukemia-free individual for anti-AML treatment, and/or
    iv) referring patients having increased levels of differentiated mesenchymal stromal cells and/or osteoblastic cells in said sample compared to levels of differentiated mesenchymal stromal cells and/or osteoblastic cells of a healthy, leukemia-free individual for anti-AML treatment.

2. The method according to claim 1, wherein said treatment is suitable for chemotherapy-resistant AML.

3. The method according to claim 1, wherein said primitive mesenchymal stromal cells are mesenchymal progenitors (CD45−31−235a−146+166−).

4. The method according to claim 1, wherein said differentiated mesenchymal stromal cells are CD45−31−235a− mesenchymal stromal cells.

5. The method according to claim 1, wherein said osteoblastic cells are CD146+31−235a−146−166+ cells.

6. The method according to claim 1, wherein said levels of primitive mesenchymal stromal cells in said sample are increased compared to levels of primitive mesenchymal stromal cells of a healthy, leukemia-free individual and said patient is referred for AML treatment within one year of said complete remission.

7. The method according to claim 1, wherein said levels of differentiated mesenchymal stromal cells and/or osteoblastic cells in said sample are increased compared to levels of differentiated mesenchymal stromal cells and/or osteoblastic cells of a healthy, leukemia-free individual and said patient is referred for AML treatment within more than one year of said complete remission.

8. The method according to claim 2, wherein said treatment comprises a treatment selected from the group consisting of radiation therapy and bone marrow transplantation.

9. A method for treating relapsed acute myeliod leukemia (AML) in a remitted patient, comprising:
   i) obtaining a bone marrow sample from said leukemia patient following complete remission from acute myeloid leukemia;
   ii) assaying cells of said bone marrow sample to determine levels of stromal cells selected from the group consisting of primitive mesenchymal stromal cells, differentiated mesenchymal stromal cells and osteoblastic cells;
   iii) initiating anti-AML treatment within a year from said complete remission wherein levels of primitive mesenchymal stromal cells in said sample are increased compared to levels of primitive mesenchymal stromal cells of a healthy, leukemia-free individual, and/or
   iv) initiating anti-AML treatment within more than one year from said complete remission wherein levels of differentiated mesenchymal stromal cells and/or osteoblastic cells in said sample are increased compared to levels of differentiated mesenchymal stromal cells and/or osteoblastic cells of a healthy, leukemia-free individual.

10. The method according to claim 9, wherein said treatment is suitable for chemotherapy-resistant AML.

11. The method according to claim 9, said treatment comprises a treatment selected from the group consisting of radiation therapy and bone marrow transplantation.

12. The method according to claim 9, wherein said primitive mesenchymal stromal cells are mesenchymal progenitors (CD45−31−235a−146+166−).

13. The method according to claim 9, wherein said differentiated mesenchymal stromal cells are CD45−31−235a− mesenchymal stromal cells.

14. The method according to claim 9, wherein said osteoblastic cells are CD146+31−235a−146−166+cells.

15. The method of claim 1, wherein said anti-AML treatment when levels of primitive mesenchymal stromal cells in said sample are increased compared to levels of primitive mesenchymal stromal cells of a healthy, leukemia-free individual comprises administering one or more inhibitors of primitive mesenchymal stromal cells.

16. The method of claim 1, wherein said anti-AML treatment when levels of differentiated mesenchymal stromal cells and osteoblastic cells in said sample are increased compared to levels of differentiated mesenchymal stromal cells and osteoblastic cells of a healthy, leukemia-free individual comprises administering one or more inhibitors of differentiated mesenchymal stromal cells and osteoblastic cells.

17. The method of claim 9, wherein said anti-AML treatment when levels of primitive mesenchymal stromal cells in said sample are increased compared to levels of primitive mesenchymal stromal cells of a healthy, leukemia-free individual comprises administering one or more inhibitors of primitive mesenchymal stromal cells.

18. The method of claim 9, wherein said anti-AML treatment when levels of differentiated mesenchymal stromal cells and osteoblastic cells in said sample are increased compared to levels of differentiated mesenchymal stromal cells and osteoblastic cells of a healthy, leukemia-free individual comprises administering one or more inhibitors of differentiated mesenchymal stromal cells and osteoblastic cells.

* * * * *